United States Patent
Poker et al.

(10) Patent No.: US 12,343,277 B2
(45) Date of Patent: *Jul. 1, 2025

(54) TLSO/LSO SPINE BRACE

(71) Applicant: DeRoyal Industries, Inc., Powell, TN (US)

(72) Inventors: Nicholas John Poker, Knoxville, TN (US); Lily Dawn Goins, Speedwell, TN (US); Dhanvin Sunil Desai, Knoxville, TN (US); John Connor Brown, Knoxville, TN (US); Charles Joseph French, III, Knoxville, TN (US); Karen M. Clements, Knoxville, TN (US); Nicholas Joseph Marquette, Knoxville, TN (US); Olufunke Tina Anjonrin-Ohu, Knoxville, TN (US)

(73) Assignee: DeRoyal Industries, Inc., Powell, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/239,179

(22) Filed: Aug. 29, 2023

(65) Prior Publication Data

US 2023/0398013 A1  Dec. 14, 2023

Related U.S. Application Data

(63) Continuation of application No. 17/304,256, filed on Jun. 17, 2021, now Pat. No. 11,771,580.

(60) Provisional application No. 63/118,070, filed on Nov. 25, 2020.

(51) Int. Cl.
*A61F 5/02* (2006.01)

(52) U.S. Cl.
CPC .............. *A61F 5/022* (2013.01); *A61F 5/028* (2013.01)

(58) Field of Classification Search
CPC .......... A61F 5/022; A61F 5/028; A61F 5/024; A61F 5/026; A61F 5/0193; A61F 5/02–03; A41D 13/0531; A61H 3/008
USPC ......................................... 224/637, 648, 649
See application file for complete search history.

(56) References Cited

U.S. PATENT DOCUMENTS

| | | | |
|---|---|---|---|
| 6,478,759 B1 * | 11/2002 | Modglin | A61F 5/028 128/100.1 |
| 10,368,626 B2 * | 8/2019 | Roque | A45F 3/04 |
| D894,042 S * | 8/2020 | Paik | D11/218 |
| 2004/0133138 A1 * | 7/2004 | Modglin | A61F 5/024 602/21 |
| 2011/0105971 A1 * | 5/2011 | Ingimundarson | A61F 5/028 602/19 |

(Continued)

OTHER PUBLICATIONS

Kun-Ku Oh, Office of the United Arab Emirates Ministry of Economy, Search Report, Application No. P6002135 / 2021, Jul. 18, 2024, Abu, Dhabi.

*Primary Examiner* — Rachael E Bredefeld
*Assistant Examiner* — Seth R. Brown
(74) *Attorney, Agent, or Firm* — Luedeka Neely, P.C.

(57) ABSTRACT

The disclosure provides a brace for supporting a spine of a patient. The brace includes an anterior panel, a posterior panel, lateral panels bridging between the anterior panel and the posterior panel, and an adjustable belt tightenable around the anterior panel, the brace selectively configurable to include either lateral panels attachable to the posterior, a posterior thoracic extension attachable to the posterior panel or a dorsal lumbar extension attachable to the posterior panel.

2 Claims, 25 Drawing Sheets

(56) References Cited

U.S. PATENT DOCUMENTS

| | | | |
|---|---|---|---|
| 2013/0184625 A1* | 7/2013 | Ingimundarson | A61F 5/026 602/19 |
| 2016/0228279 A1* | 8/2016 | Modglin | A61F 5/028 |
| 2019/0029866 A1* | 1/2019 | Stier | A61F 5/026 |
| 2019/0070033 A1* | 3/2019 | Heronen | A61F 5/026 |
| 2020/0268543 A1* | 8/2020 | Santaniello | A61F 5/028 |

* cited by examiner

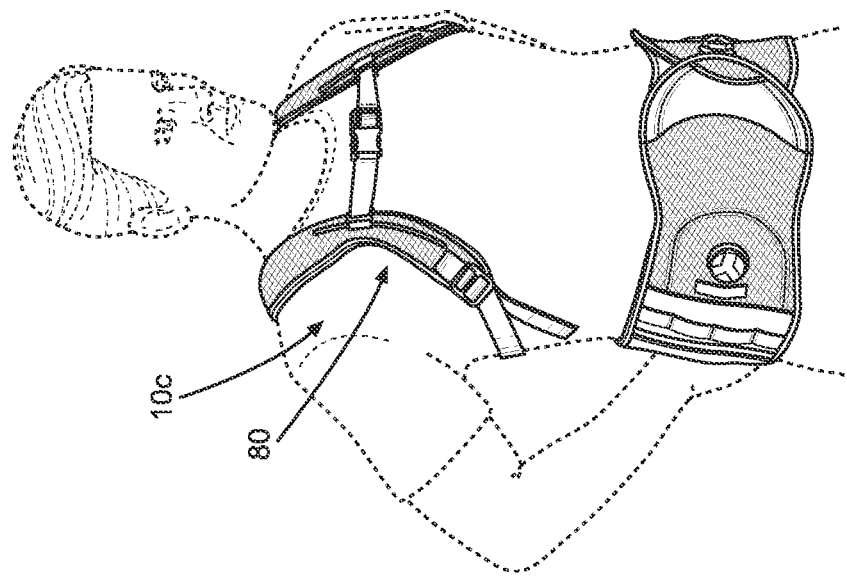
FIG. 4 TLSO-D
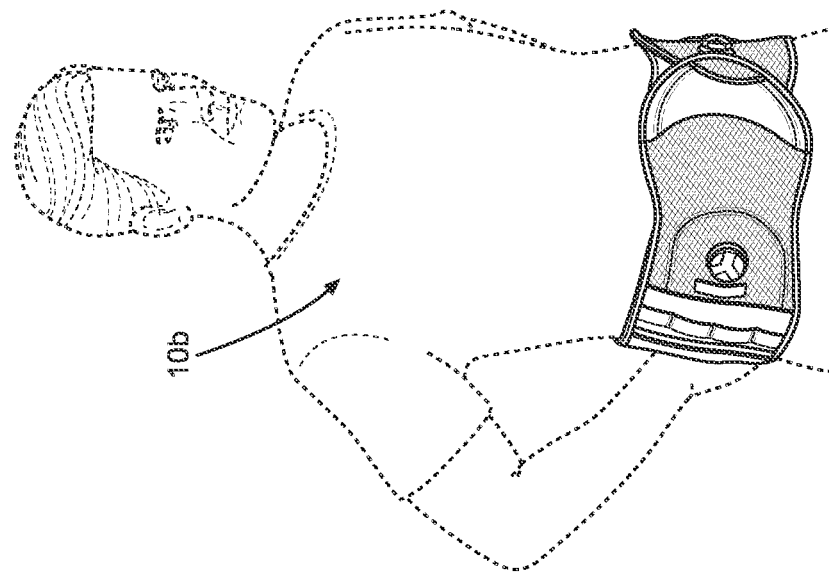
FIG. 3 LSO
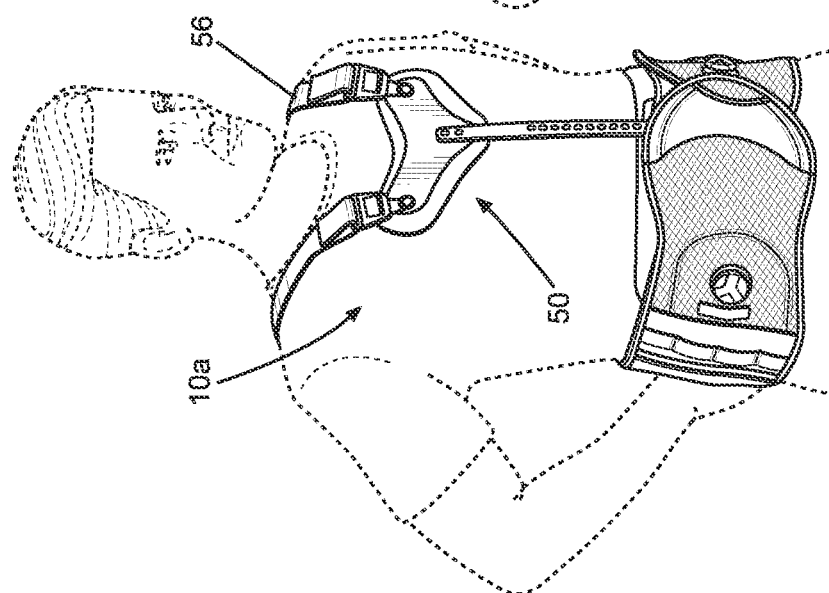
FIG. 2 TLSO-S

TLSO-S

LSO

LSO

LSO

LSO

TLSO-D

TLSO-D

TLSO-D

TLSO-D

TLSO/LSO SPINE BRACE

FIELD

The present disclosure relates to braces for the spine. More particularly, the disclosure relates to improved lumbar-sacral orthosis and thoracic-lumbar-sacral orthosis for supporting a patient's back and spine that enables multiple configurations utilizing combinations of the same base components.

BACKGROUND

Improvement is desired in the design of braces for the spine. In particular what is desired is improvements in spinal braces and improved structures that are configurable for use as a Lumbar-Sacral Orthosis (LSO) and a Thoracic-Lumbar-Sacral Orthosis (TLSO).

SUMMARY

The disclosure advantageously provides a brace system that is configurable in multiple brace configurations for supporting a spine of a patient.

In one aspect, a brace according to the disclosure includes an anterior panel; a posterior panel, a pair of lateral panels bridging between the anterior panel and the posterior panel; and an adjustable belt tightenable around the anterior, posterior, and lateral panels. The brace is selectively configurable to include the pair of lateral panels attachable to the posterior, a posterior thoracic extension attachable to the posterior panel or a dorsal lumbar extension attachable to the posterior panel.

In another aspect, a brace system according to the disclosure includes removable lateral panels, an adjustable waist belt, a removable anterior panel, a sternal pad removably attachable to and adjustable in height relative to the anterior panel, and a posterior panel having a removable posterior thoracic extension, and a removable dorsal lumbar extension.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein:

FIGS. 2-4 show the brace configured in three different configurations according to the disclosure. FIG. 2 shows the brace configured as a Thoracic-Lumbar-Sacral Orthosis with a sternal pad (TLSO-S); FIG. 3 shows the brace configured as a Lumbar-Sacral Orthosis (LSO); and FIG. 4 shows the brace configured as a Thoracic-Lumbar-Sacral Orthosis with a dorsal lumbar extension (TLSO-D).

DETAILED DESCRIPTION

With reference to the drawings, the disclosure provides a spinal brace system 10 of improved construction and configured to provide multiple configurations of spinal braces. In particular, the spinal braces provided by the spinal brace system 10 are configurable to be used as a Lumbar-Sacral Orthosis (LSO) and two different Thoracic-Lumbar-Sacral Orthosis (TLSO) configurations, one having a sternal pad (TLSO-S) and the other having a dorsal lumbar extension (TLSO-D).

The spinal braces according to the disclosure are particularly configured to provide support and immobilization in the sagittal, coronal and/or transverse planes to aid in the relief and recovery from postoperative fusion, postoperative laminectomy, postoperative discectomy, compression fractures, degenerative disc disease, osteoporosis, chronic low back pain, spondylolisthesis, spondylolysis, spinal stenosis, spinal osteoarthritis, and facet syndrome.

Figure 1:
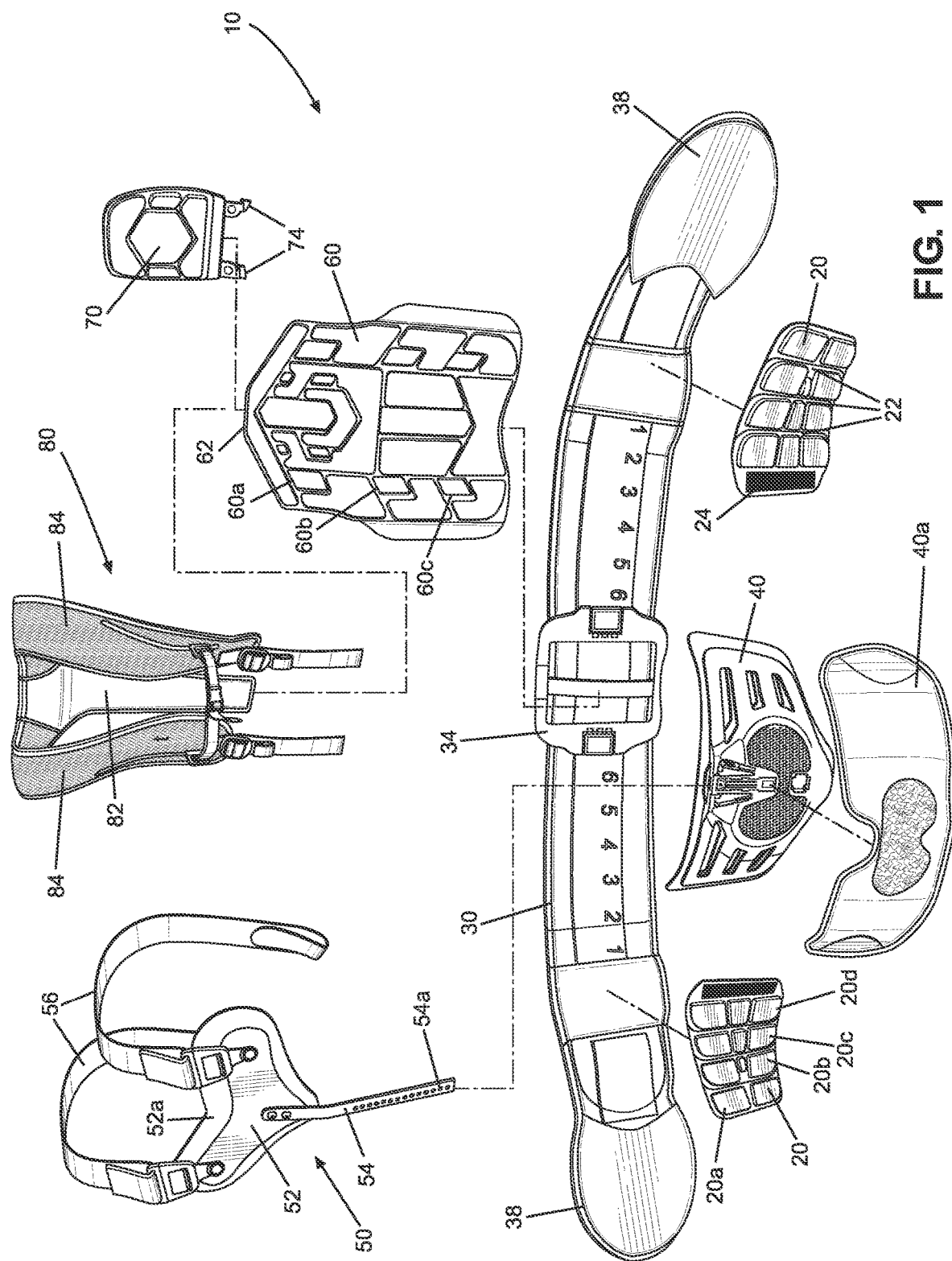
FIG. 1 is an exploded perspective view showing components of a brace for the spine according to the disclosure.
Figure 5A:
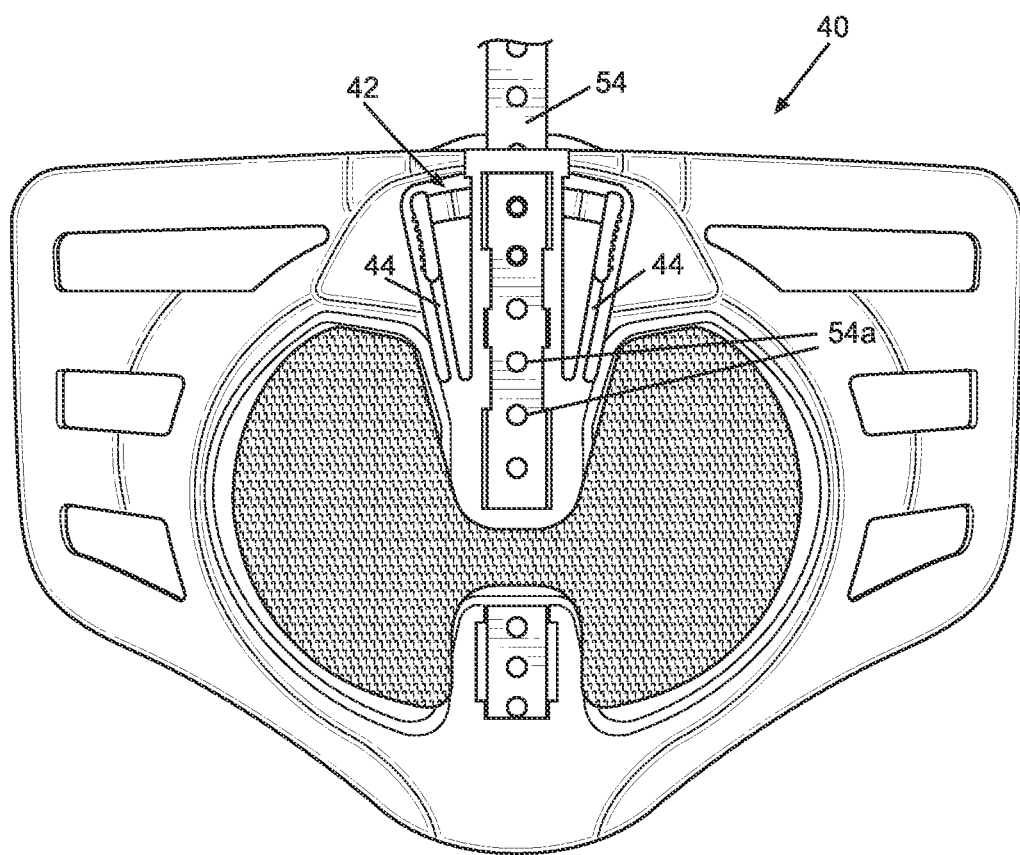
FIGS. 5A-5D are detailed views of height adjustment structure for adjusting the height of a sternal pad component of the brace system.
Figure 5B:
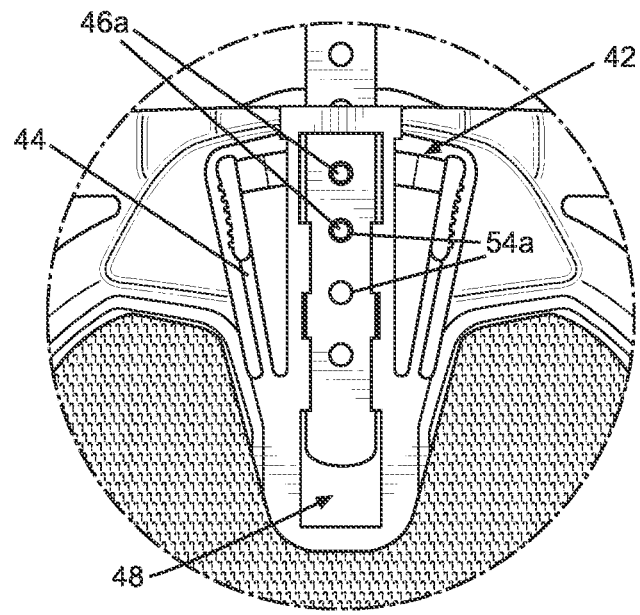
Figure 5C:
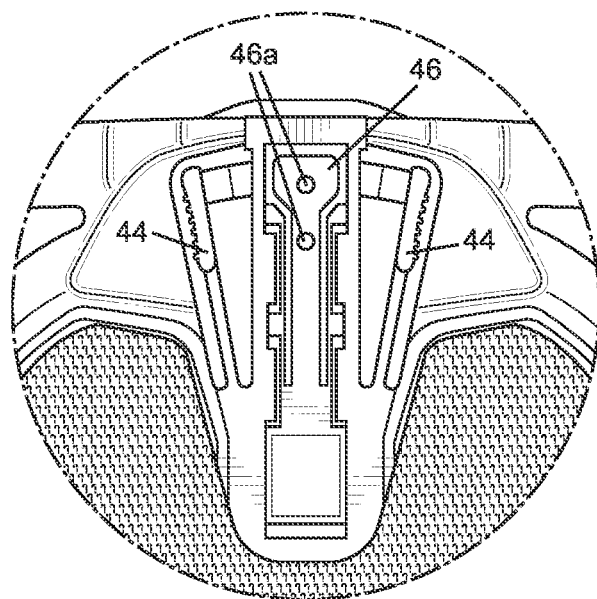
Figure 5D:
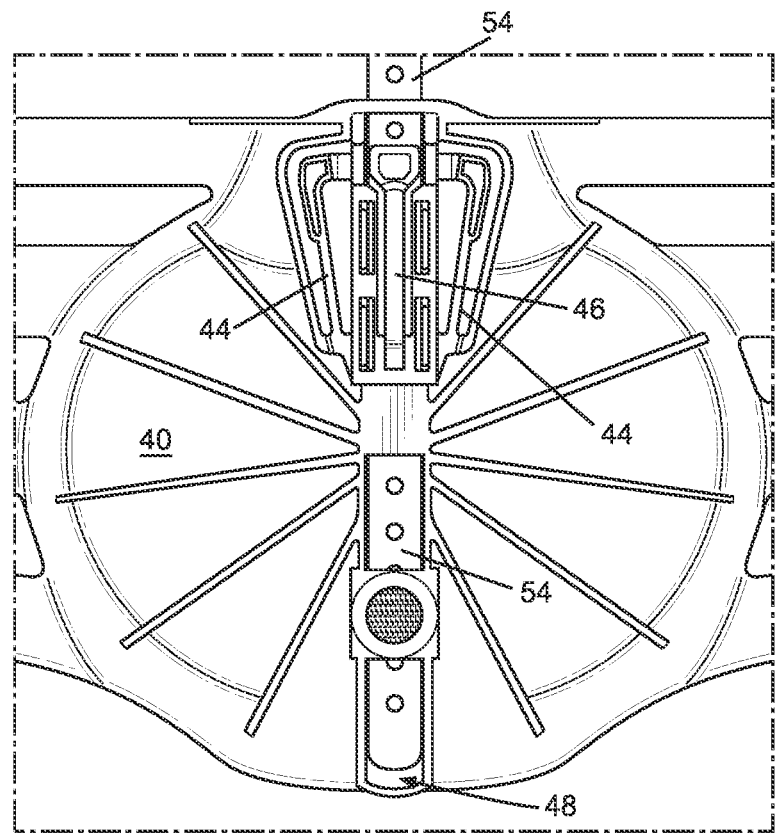

With initial reference to FIG. 1, the spinal brace system 10 includes components that may be selectively utilized in various combinations to provide the desired brace configuration most optimal for the patient's injury. For example, as shown, the spinal brace system 10 includes as selectable components: trimmable lateral panels 20, an adjustable belt 30, an anterior panel 40 having a sternal pad kit (SPK) 50, and a posterior panel 60 having a removable posterior thoracic extension (PTE) 70, and a removable dorsal lumbar extension (DLE) 80.

The lateral panels 20, the posterior panel 60 and the posterior thoracic extension 70 are made of injection molded plastic and compressed foam. Thus, in combination with the adjustable belt 30, when a brace according to the disclosure is applied about the patient will compress around the midsection of the patient to offer stabilization to the spinal column.

By selective use of the components 20-80, the spinal brace system 10 is convertible between three different spinal brace configurations. A TLSO-S spinal brace configuration 10a is shown in FIG. 2 and FIGS. 8A-8D. An LSO spinal brace configuration 10b is shown in FIG. 3 and FIGS. 9D and 10A-10C. A TLSO-D spinal brace configuration 10c is shown in FIG. 4 and FIGS. 11B and 12A-12B.

Figure 11A:
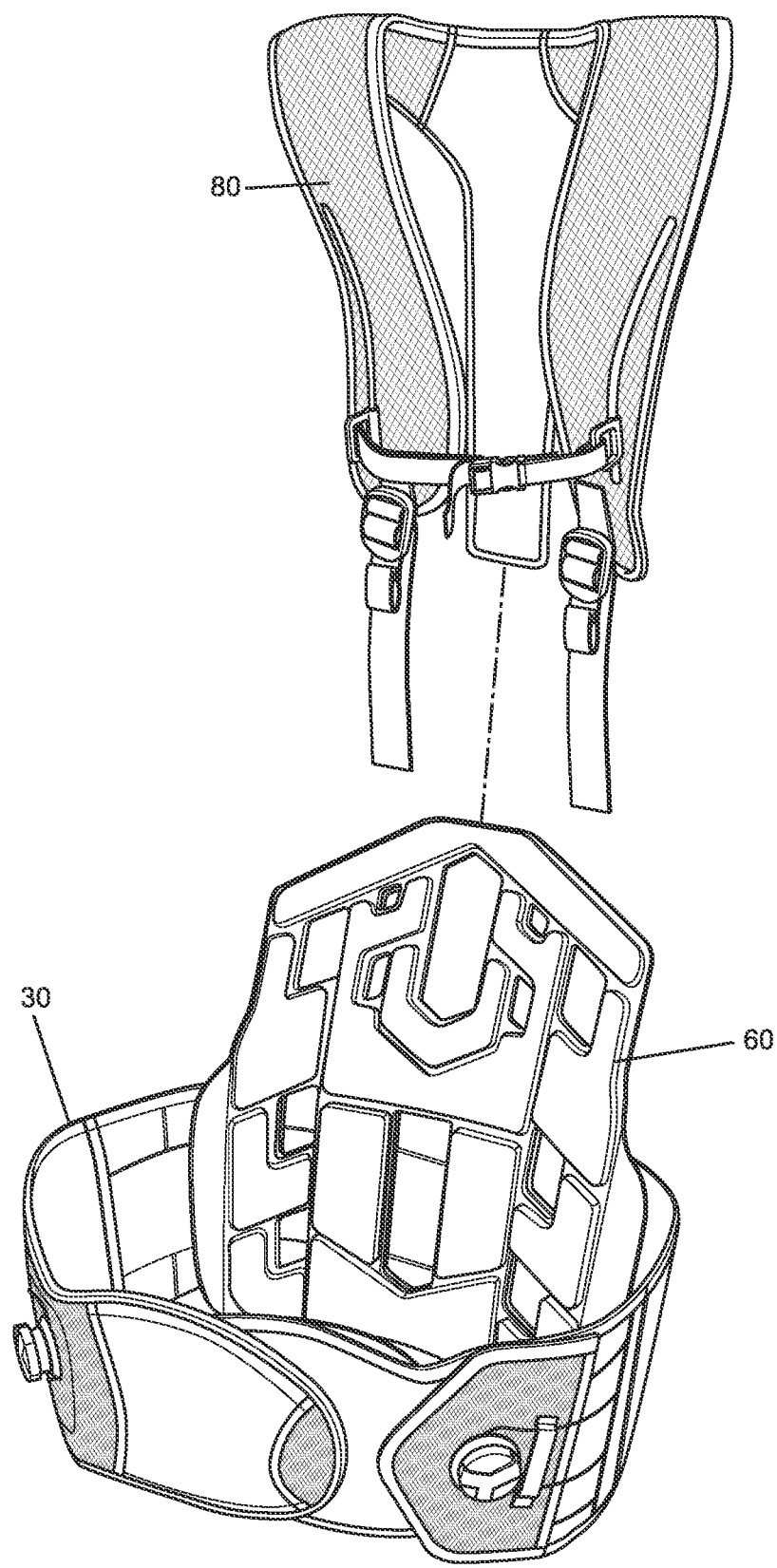
FIGS. 11A-11B show conversion of the brace from the LSO configuration to the TLSO-D configuration.
Figure 11B:
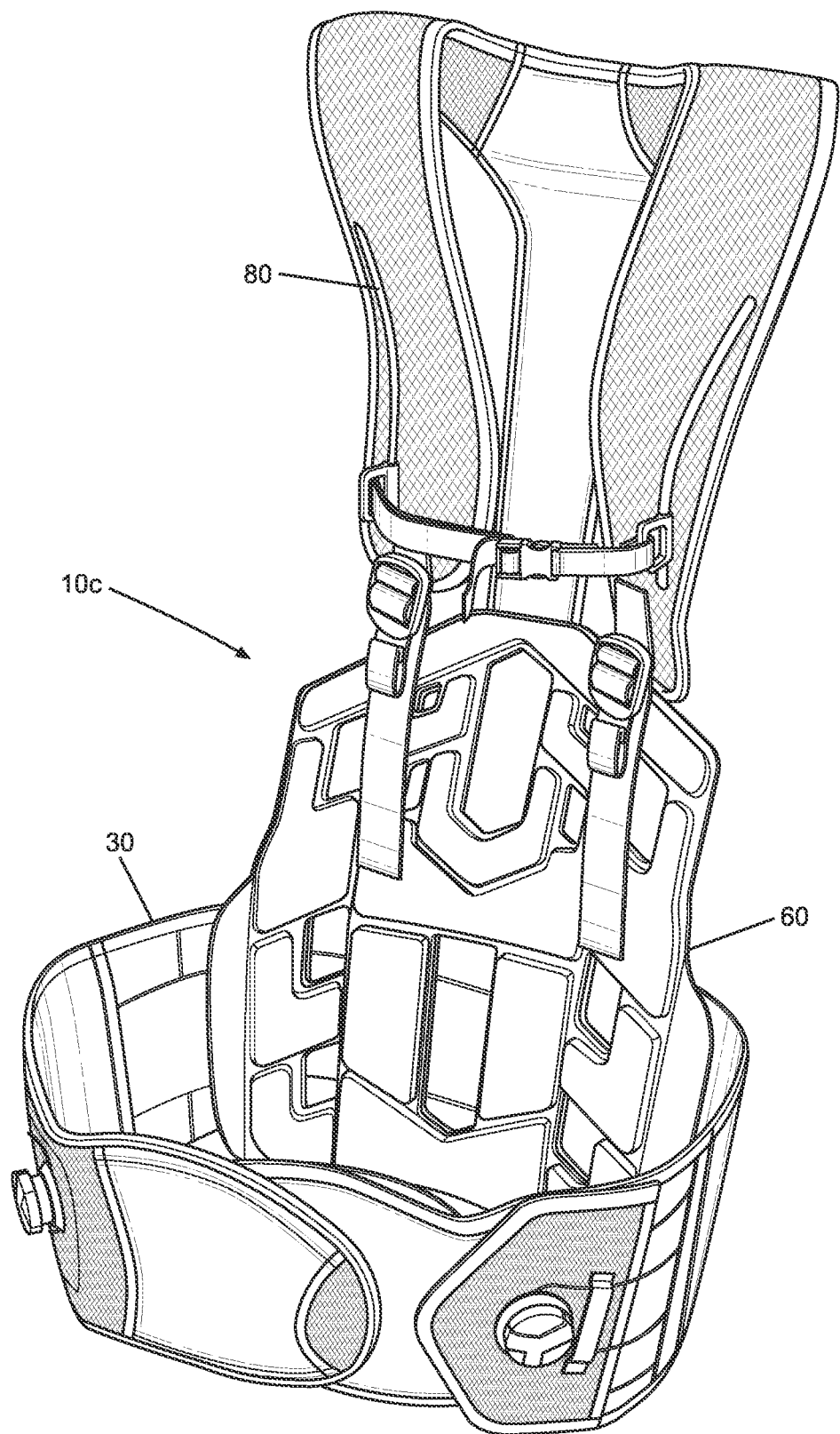

As discussed in detail below, FIGS. 9A-9D show conversion from the TLSO-S configuration to the LSO configuration. FIGS. 11A-11B show conversion from the LSO configuration to the TLSO-D configuration.

Returning to FIG. 1, the trimmable lateral panels 20 have panel segments 20a, 20b, 20c and 20d joined by trim guides 22. The trim guides 22 are configured as thin demarcations between the panel segments that are easy to cut and follow during cutting. A hook/loop material 24 may be provided on the proximal ends of the panels 20 for releasable attachment of the lateral panels 20 to the posterior panel 60.

Figure 13A:
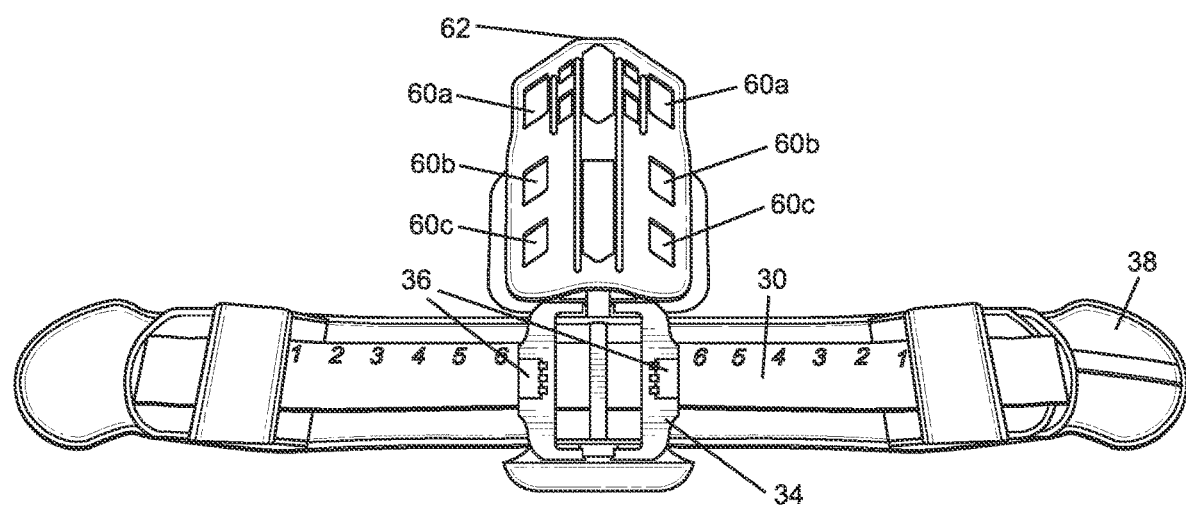
FIGS. 13A-13D show structures for adjusting the length of a belt component of the brace system.
Figure 13B:
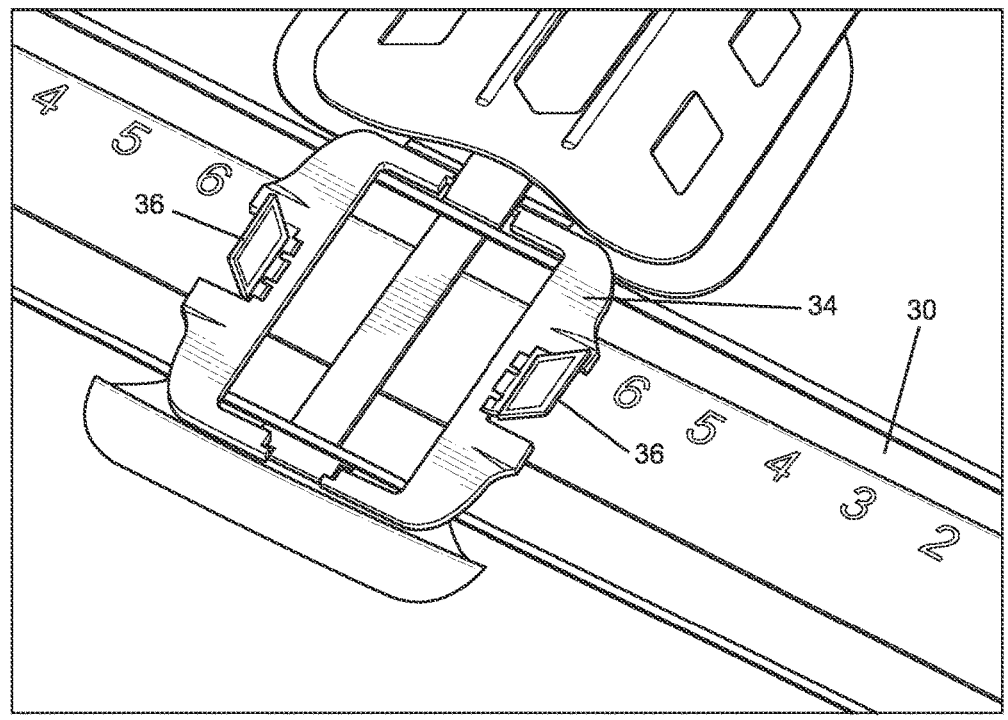
Figure 13C:
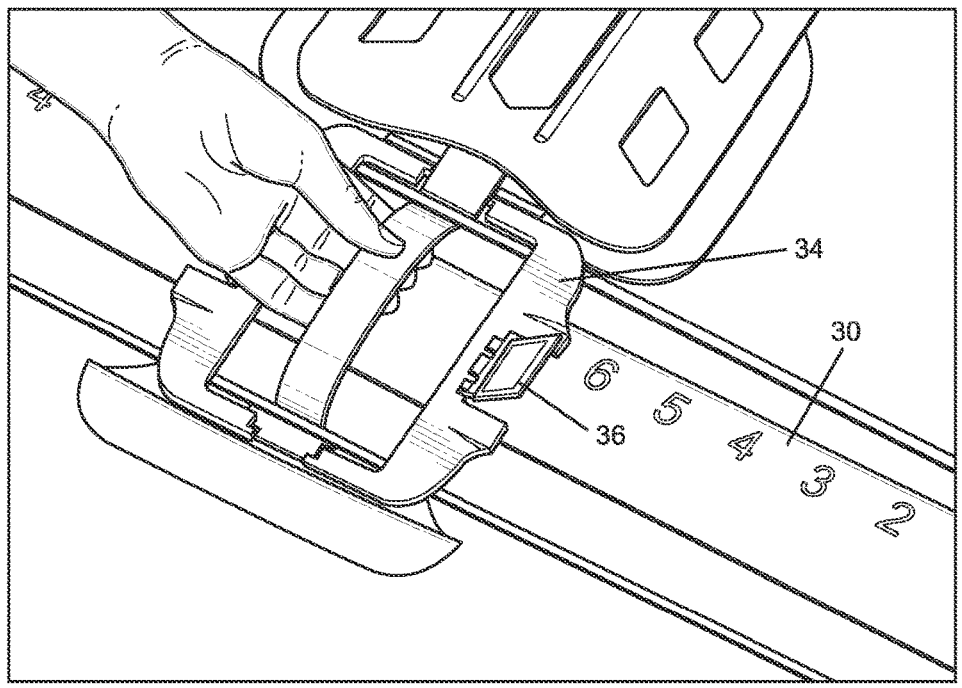
Figure 13D:
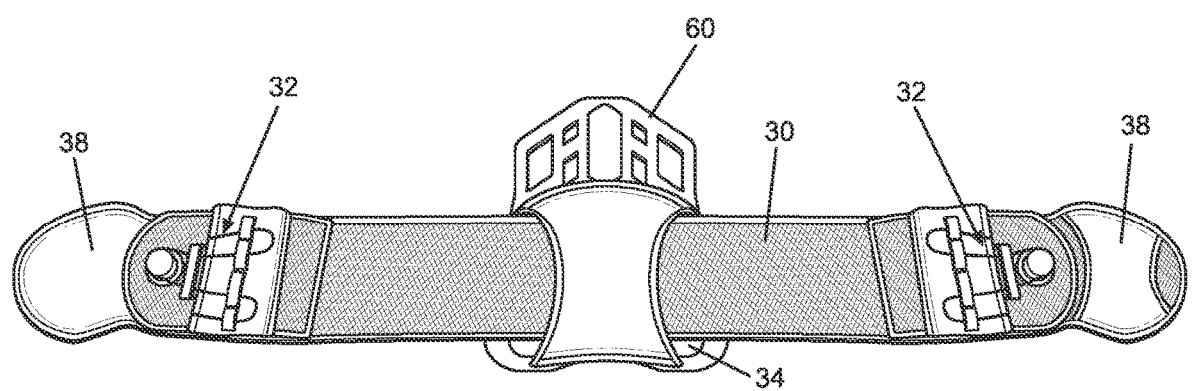

As best seen in FIG. 13D, the adjustable belt 30 has cable tensioners 32, such as cable reels available under the name BOA from Boa Technology, Inc. of Denver, Colorado. The cable tensioners 32 facilitate snug fitting of the belt once the desired length of the belt is achieved.

To adjust the length of the belt 30, an adjustment plate 34 is provided having spaced apart belt passage slits through which the belt 30 is passed and belt engagement members 36 that are pivotally adjustable relative to the plate to engage or disengage the belt 30. The belt engagement members 36 are engaged with the belt to maintain a desired length of the brace, and are disengaged from the belt to permit adjustment of the length of the brace. A soft fabric plate cover 34a is attached to the back of the plate 34 and the belt 30 as by mating hook/loop material. An exemplary adjustment plate 34 may be provided by the adjustment plate structure described in U.S. Pat. No. 10,143,582 entitled ADJUSTABLE BACK BRACE, assigned to DeRoyal Industries, Inc. and incorporated herein by reference in its entirety.

The belt 30 also has belt ends 38. The ends 38 may be of fixed position or may be removable and adjustably positionable as by hook/loop materials at the ends of the belts 30. By positioning the ends 38 as desired, the belt 30 may be further custom fit so as to be a desired length. Once the desired belt length is selected, a desired tension of the belt 30 is achieved by use of the cable tensioners 32. Also, a spanning segment may be utilized to span between the ends 38 if the girth of the patient is such that the ends 38 cannot be positioned to overlap. The spanning segment may be removably positionable to the ends 38 or the belt 30 as by hook/loop material.

With reference to FIGS. 5A-5D the anterior panel 40 has an integrated adjustable mount 42 for adjustably mounting the sternal pad kit 50 onto the anterior panel 40. The mount 42 includes wedged levers 44 operatively associated with a retaining arm 46 having pins 46a and located within a channel 48. An anterior panel cover 40a provided by a soft loop material attaches to anterior panel 40 using hook material. The cover 40a provides a surface that is soft and to which hook material associated with the belt 30 may adjustably attached.

Figure 8A:
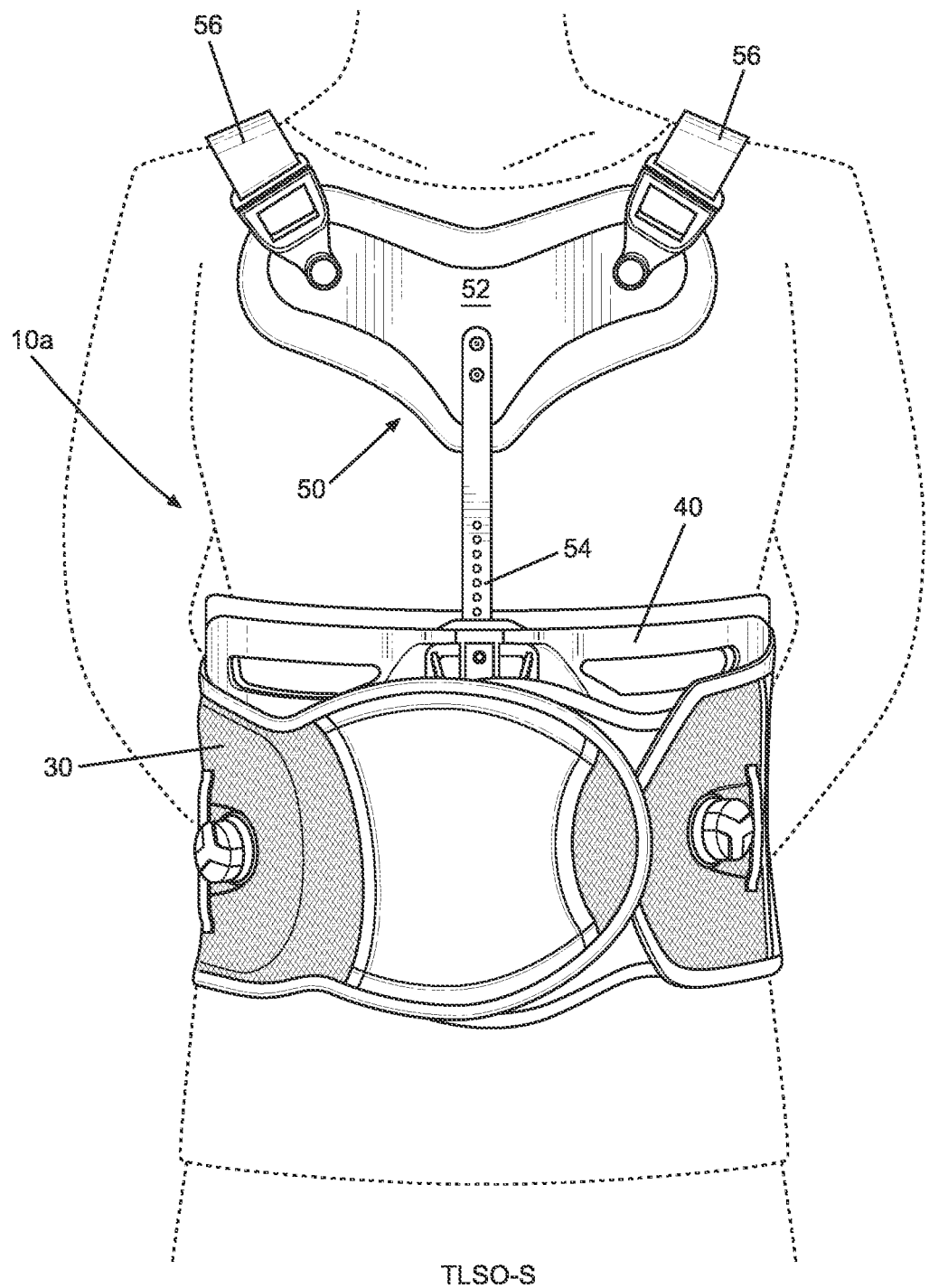
FIGS. 8A-8D show the brace in the TLSO-S configuration.
Figure 8B:
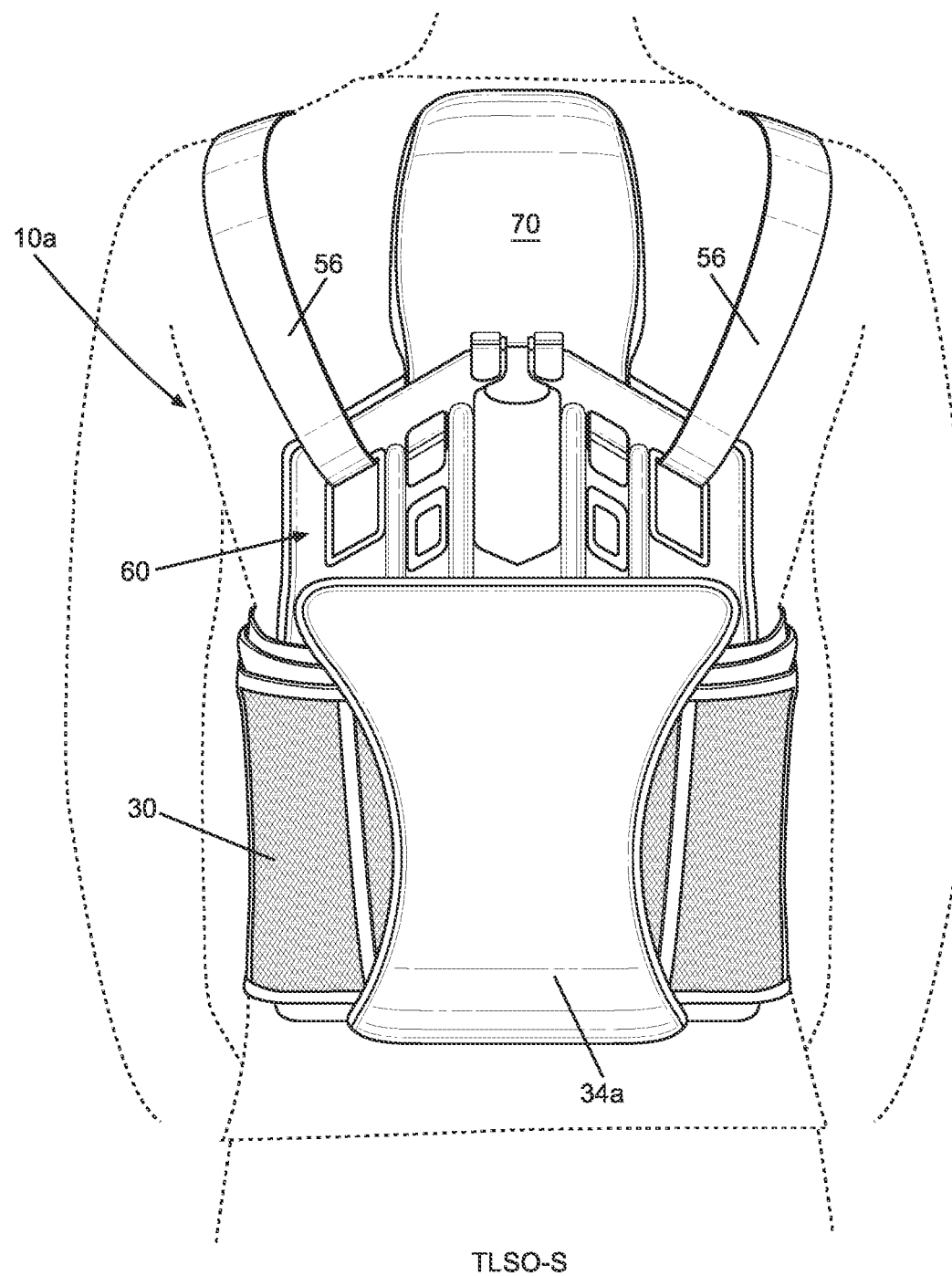
Figure 8C:
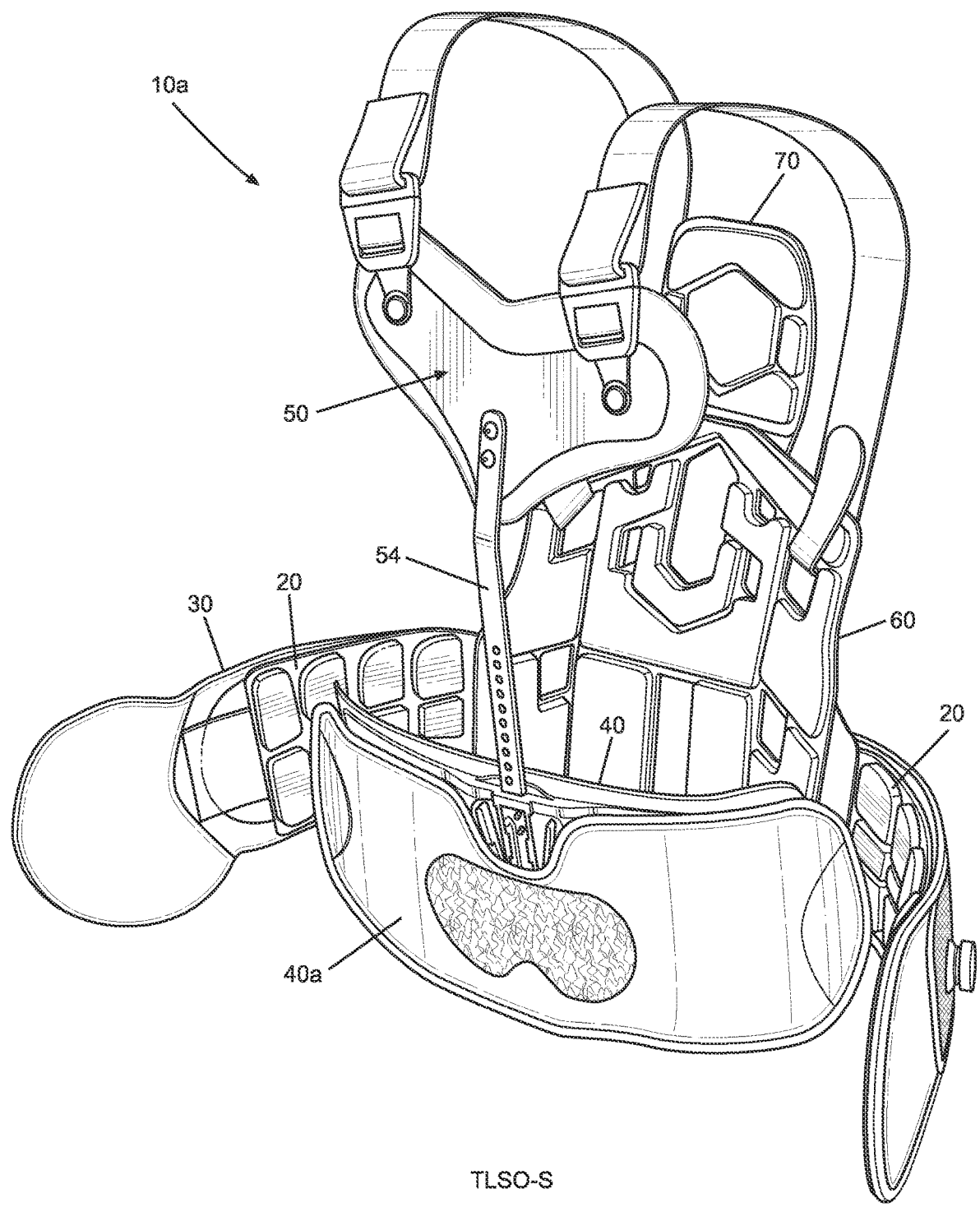
Figure 8D:
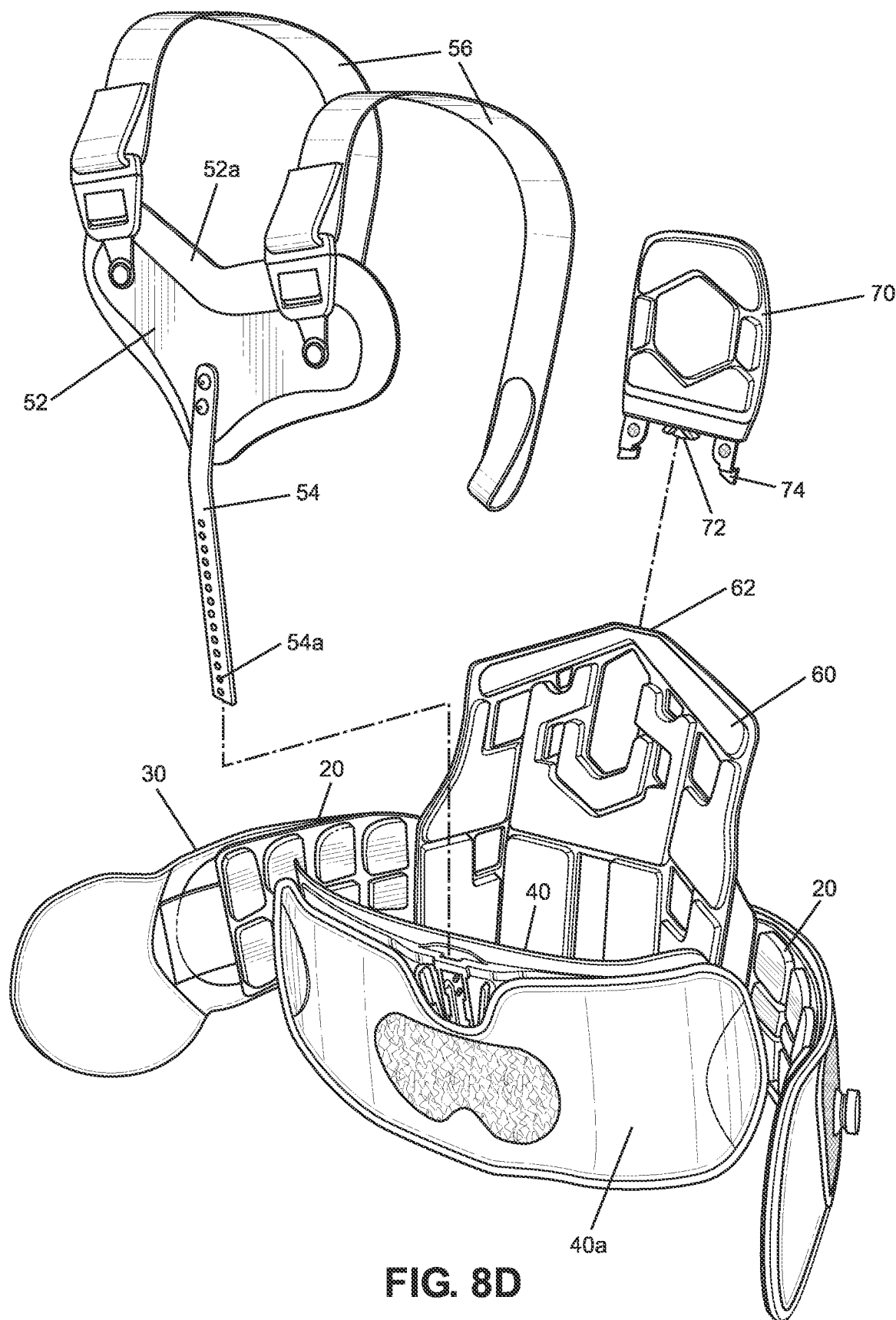
Figure 9A:
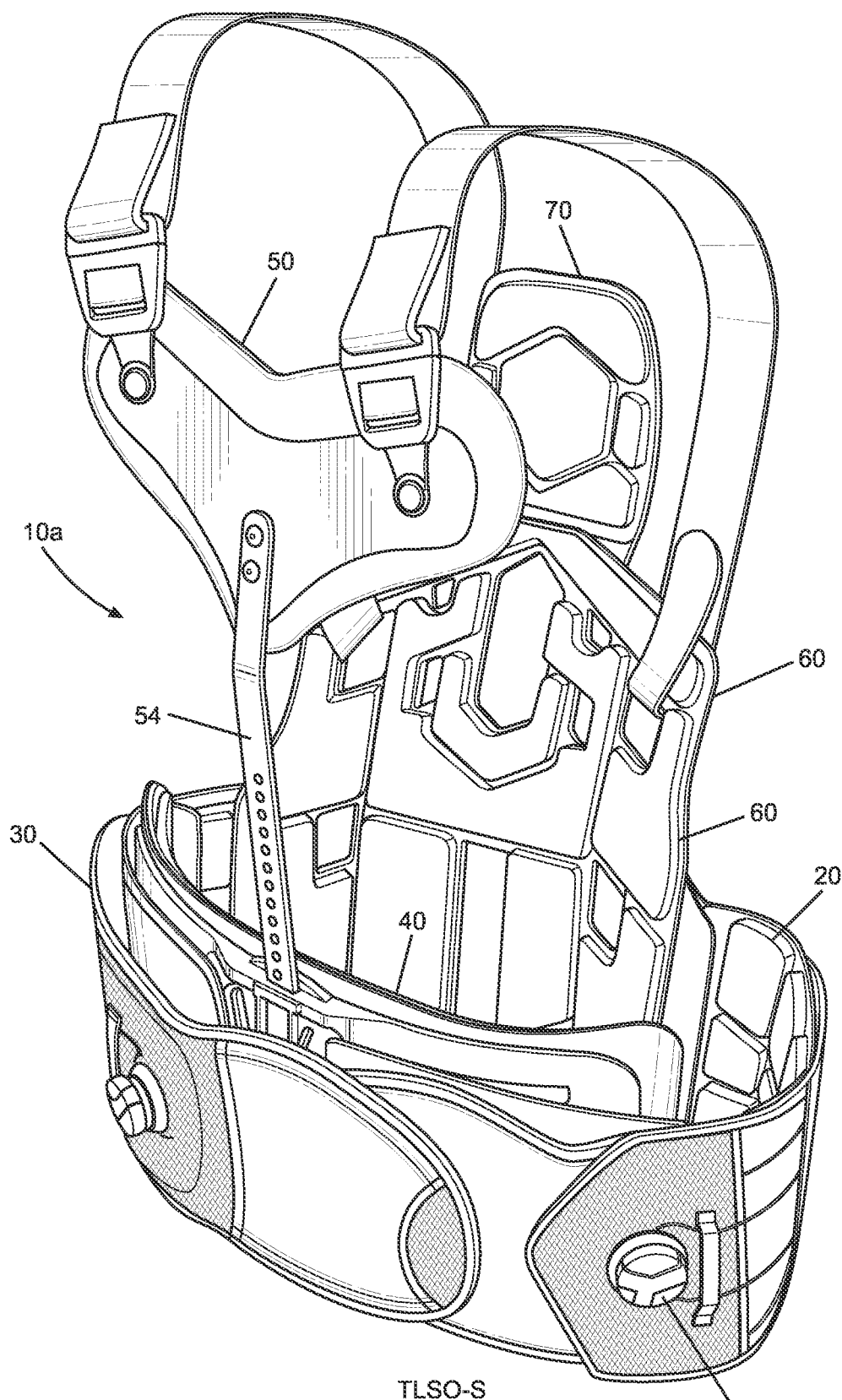
FIGS. 9A-9D show conversion of the brace from the TLSO-S configuration to the LSO configuration.
Figure 9B:
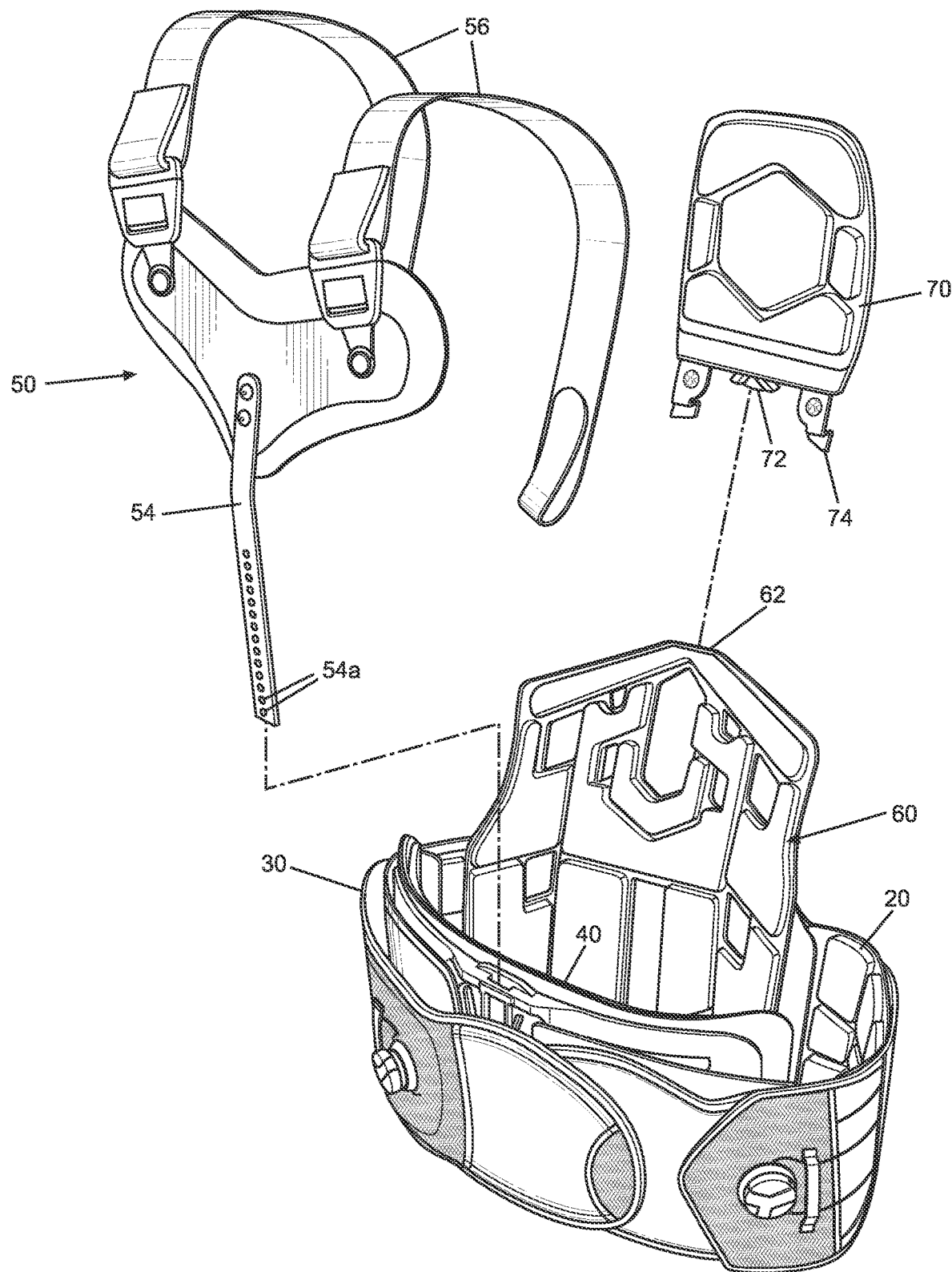
Figure 9C:
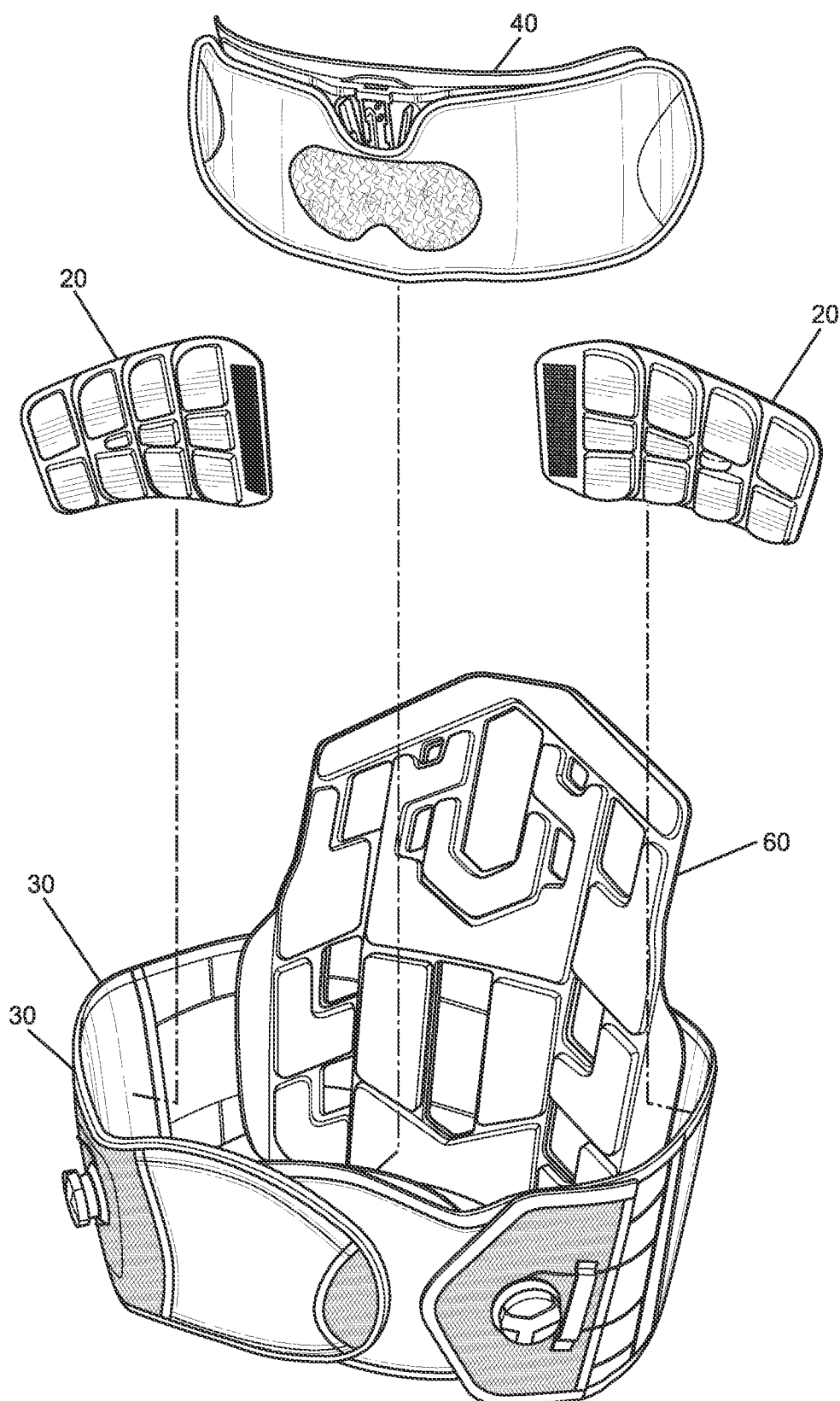
Figure 9D:
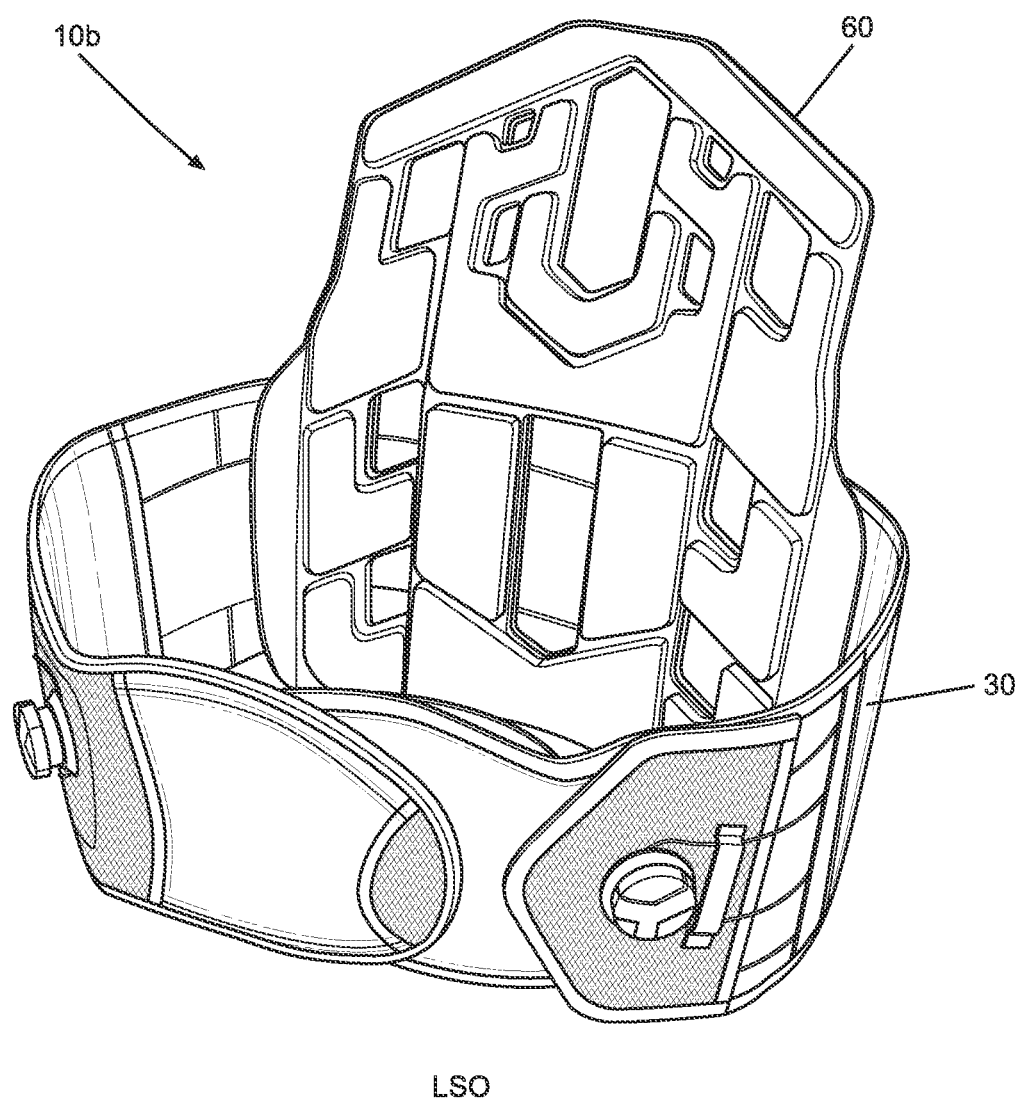

With reference to FIGS. 1 and 8D, the sternal pad kit 50 has a sternal plate 52 having a pad 52a supported by an adjustment post 54 having adjustment apertures 54a. The post 54 is received in the channel 48 of the adjustable mount 42 of the anterior panel 40. Shoulder straps 56 may be attached to the posterior of the brace as explained below.

Returning to FIGS. 5A-5D, to insert and adjust the height of the sternal pad 52, a user will pinch the wedged levers 44 and this motion will move the retaining arm 46 and pins 46a out of position. An advantage of this design is that the wedged levers 44 will bottom out or run out of travel. Thus, the retaining arm 46 can only travel back so far, and will not enter permanent deformation. When the levers 44 are released the pin 46a will be fully inserted through the apertures 54a, making failure less likely to occur.

As best seen in FIGS. 1, 6A, 7B and 13A, the posterior panel 60 is a rigid panel locatable at the posterior of a wearer of the brace adjacent the spine of the wearer. The posterior panel 60 includes a central flattened apex 62 configured for releasably receiving the posterior thoracic extension 70. The posterior panel 60 includes apertures 60a, 60b, and 60c stacked along opposite sides thereof. As describe below, the apertures 60a-60c enable anchor points for adjustably anchoring straps associated with the dorsal lumbar extension 80. Likewise, the shoulder straps 56 of the sternal pad kit 50 may be adjustably anchored to the apertures 60a-60c.

Figure 6C:
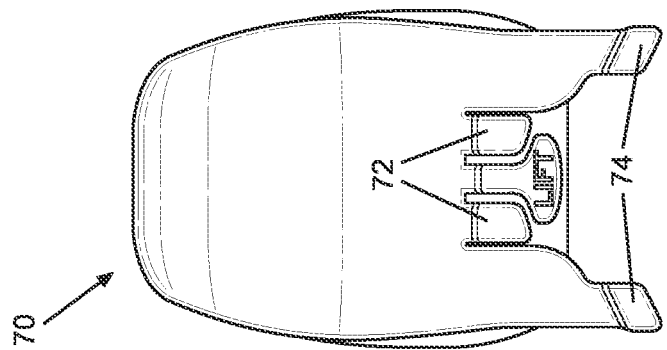
FIGS. 6A-6C are detailed views of a posterior thoracic extension component of the brace system.
Figure 6B:
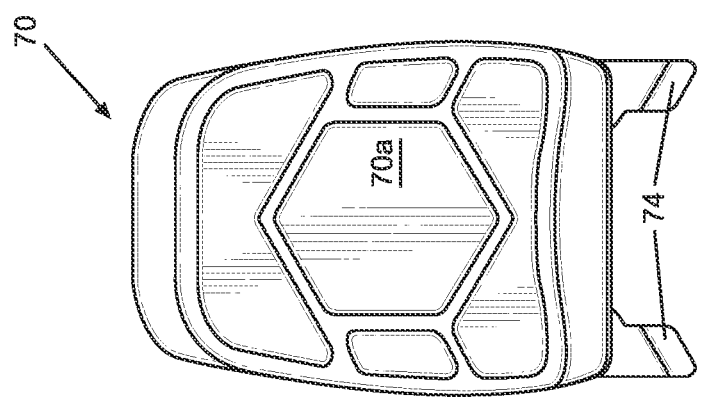
Figure 6A:
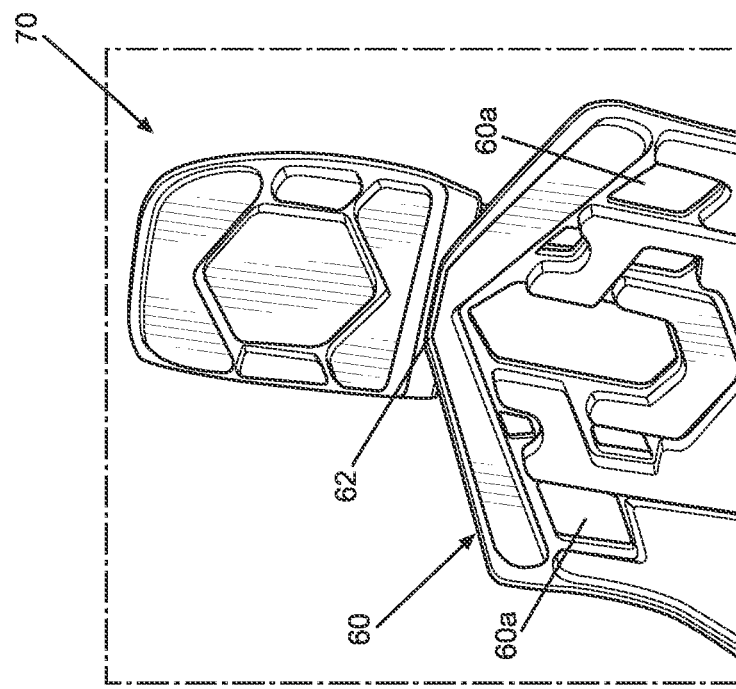

With reference to FIGS. 6A-6C, the posterior thoracic extension 70 has a padded surface 70a, central clips 72 and lateral oppositely facing elongate clips 74. The central clips 72 and elongate clips 74 cooperate with the flattened apex 62 for releasable mounting of the posterior thoracic extension 70 to the posterior panel 60.

Figure 7A:
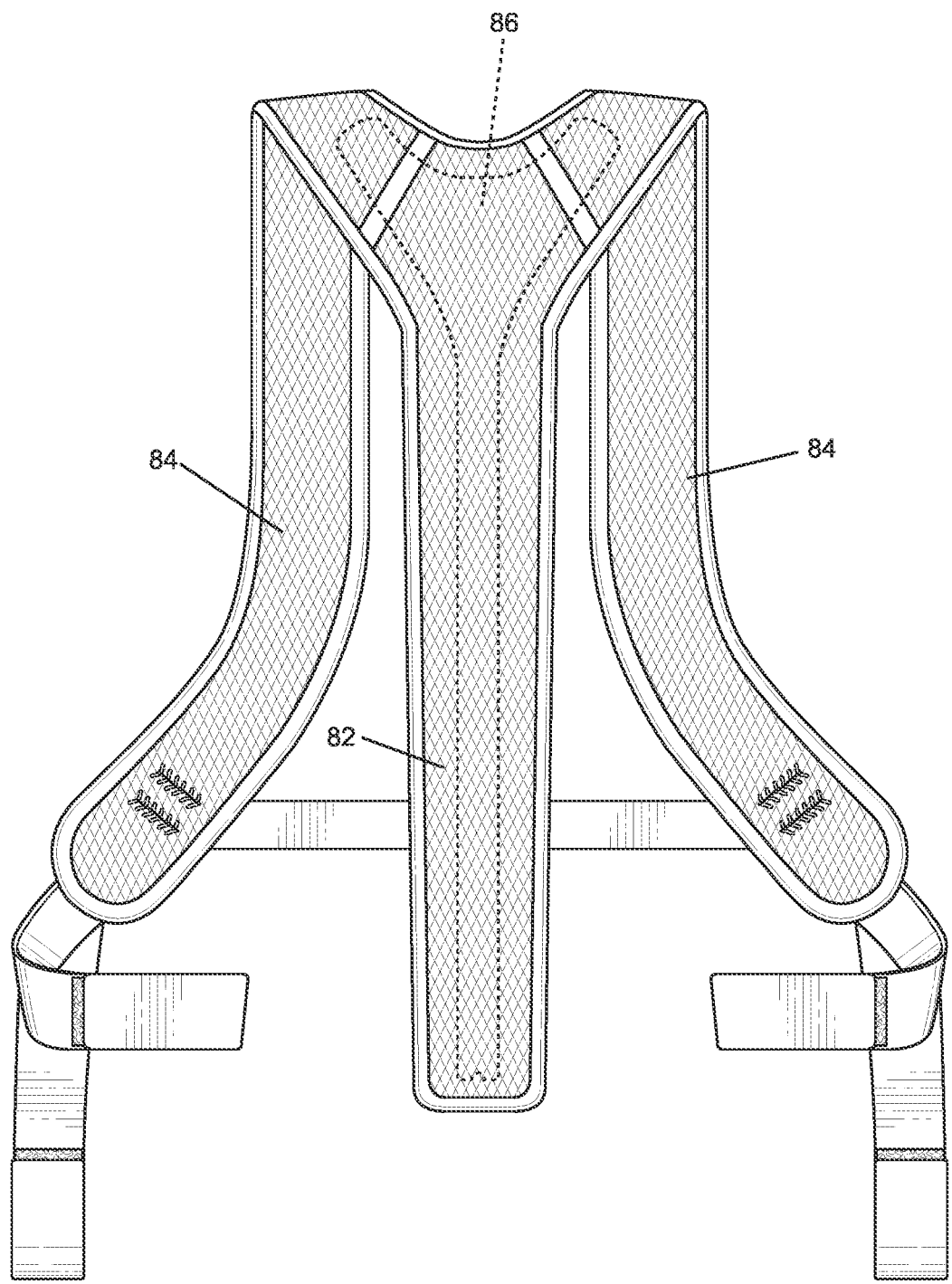
FIGS. 7A-7C are detailed views of a dorsal lumbar extension component of the brace system.
Figure 7C:
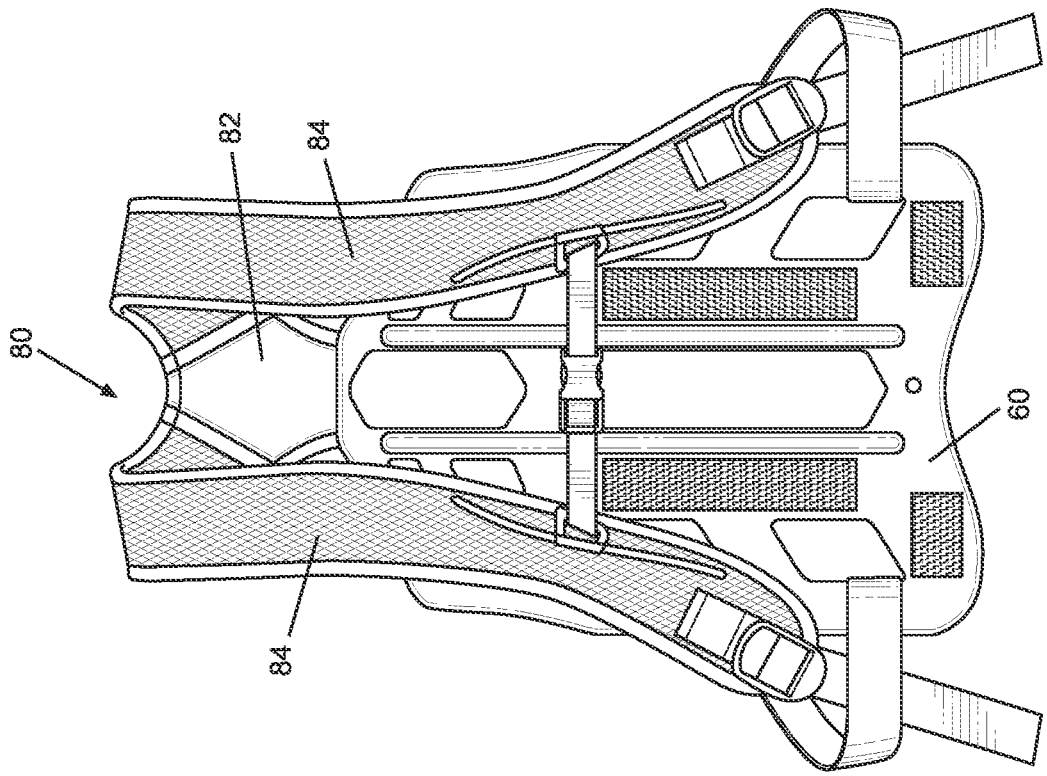
Figure 7B:
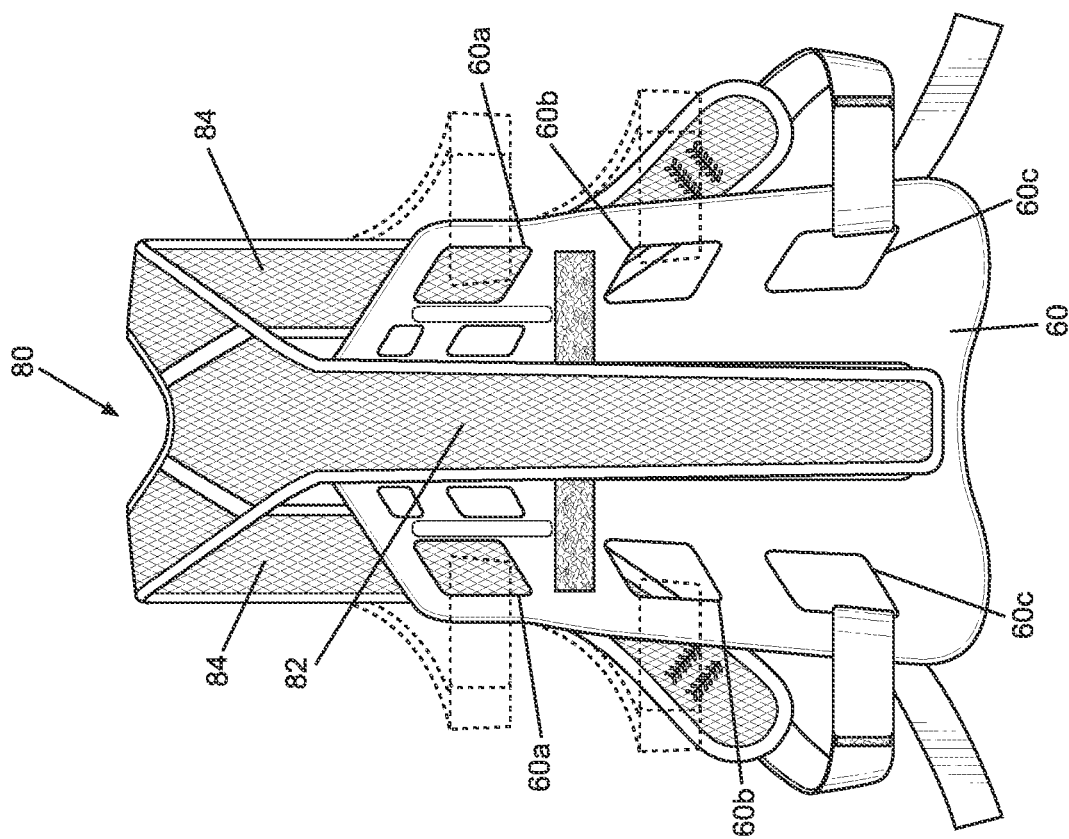

The dorsal lumbar extension 80 creates a high degree of thoracic spine immobilization. With reference to FIGS. 7A-7C, the extension 80 includes an attachment arm 82 that secures to the back of the posterior panel 60 as by hook/loop material. The dorsal lumbar extension 80 also includes straps 84 that may be anchored in any of the apertures 60a-60c which serve as anchor points for the straps 84. The adjustable nature of these anchor points 60a-60c offer the clinician the ability to optimize the amount of motion restriction, and comfort of the brace to end user, and ease of donning and doffing the brace. The dorsal lumbar extension 80 also includes an internal rigid stay 86, preferably of plastic.

FIGS. 8A-8D show components of the brace system 10 configured to provide the TLSO-S spinal brace configuration 10a, which includes the sternal pad kit 50, the anterior panel 40, the posterior panel 60, the posterior thoracic extension 70, and lateral panels 20. The brace configuration may be adjusted to match the patient's progression through recovery. For example, the sternal pad kit 52 may be removed from the TLSO-S spinal brace configuration 10a to give the patient a larger range of motion.

FIGS. 9A-9D show conversion from the TLSO-S spinal brace configuration 10a spinal brace to the LSO configuration 10b. As depicted, the conversion steps include removal of the sternal pad kit 50 and the posterior thoracic extension 70, followed by removal of the lateral panels 20 and the anterior panel 40.

Figure 10A:
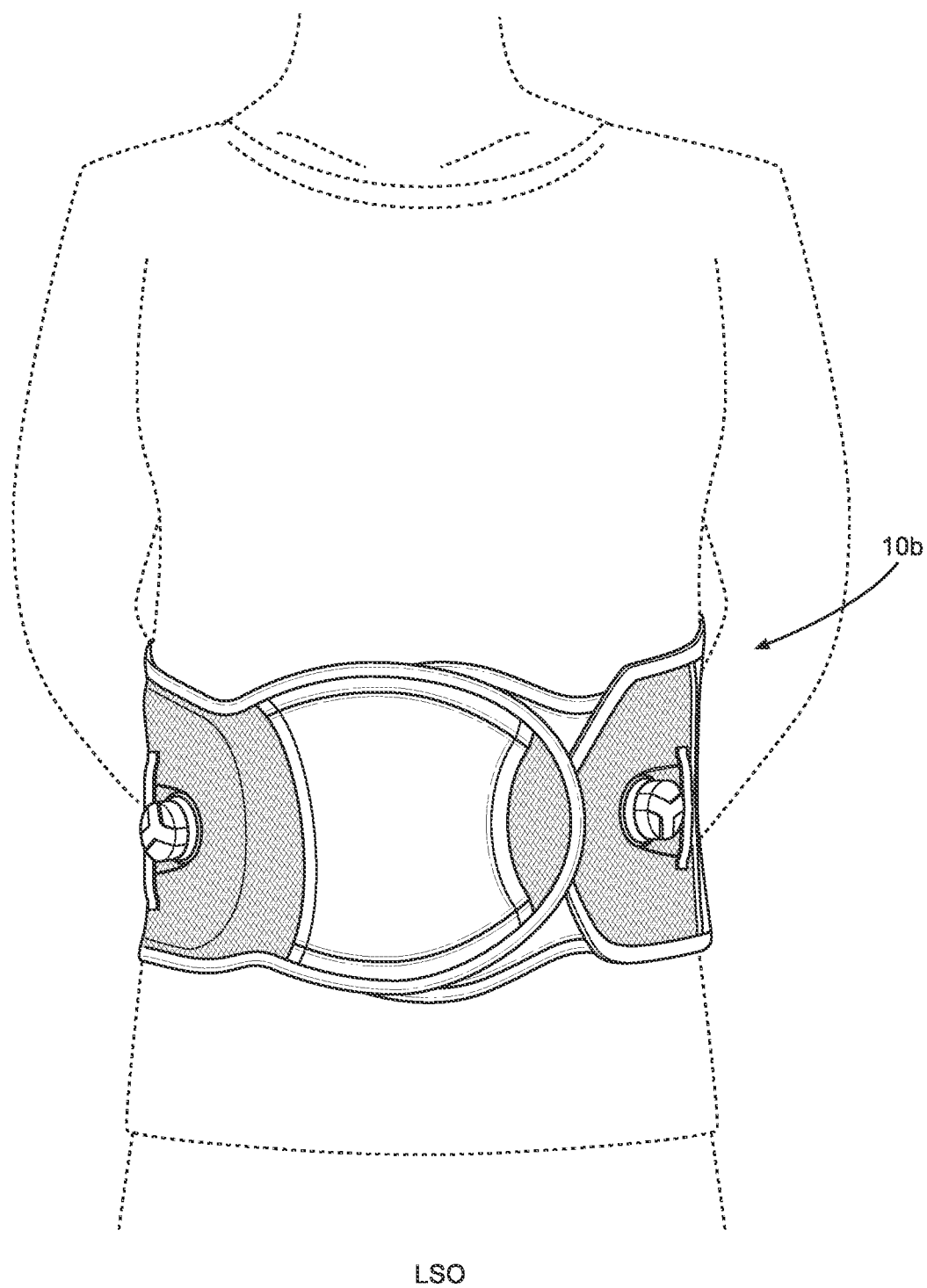
FIGS. 10A-10C show the brace in the LSO configuration.
Figure 10B:
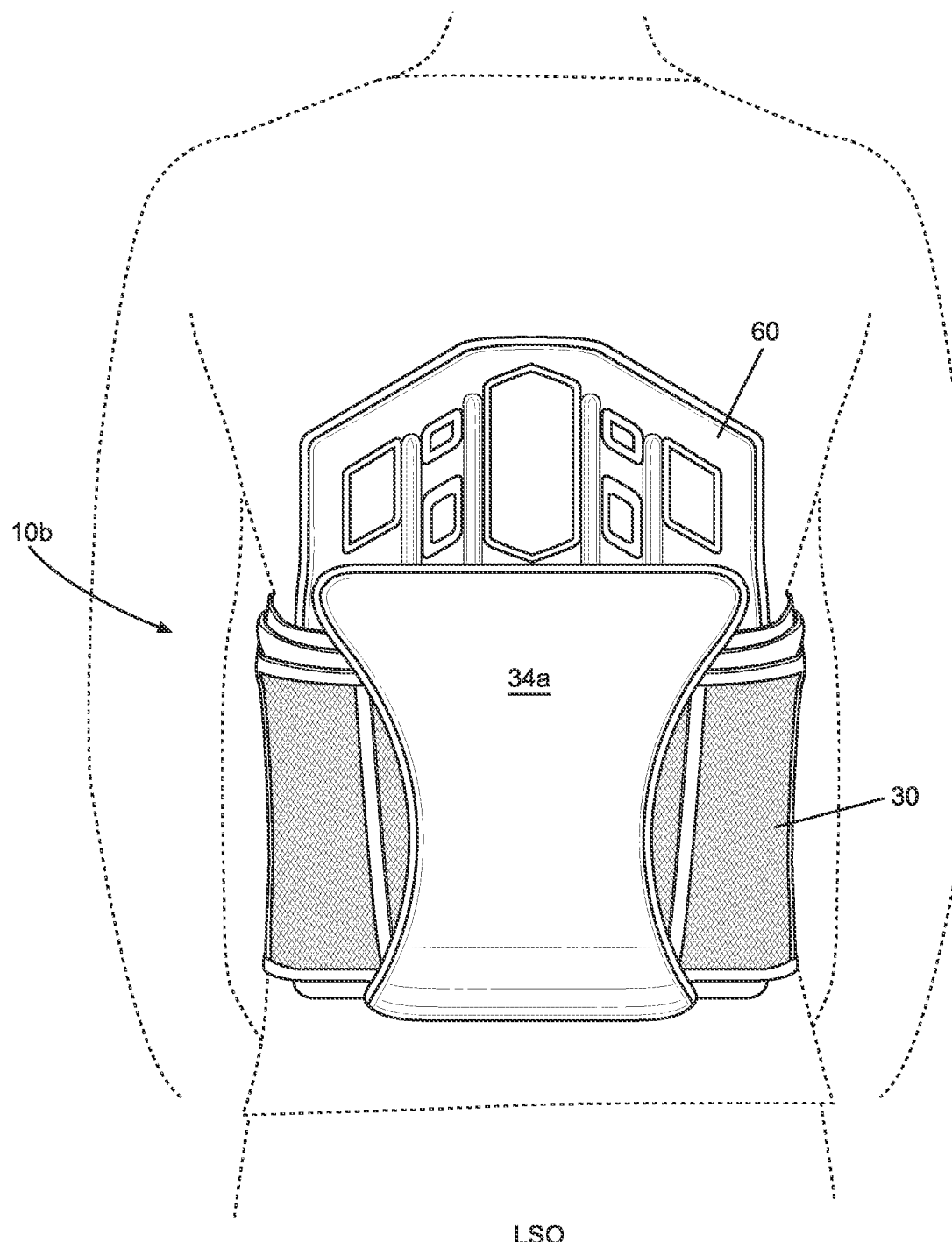
Figure 10C:
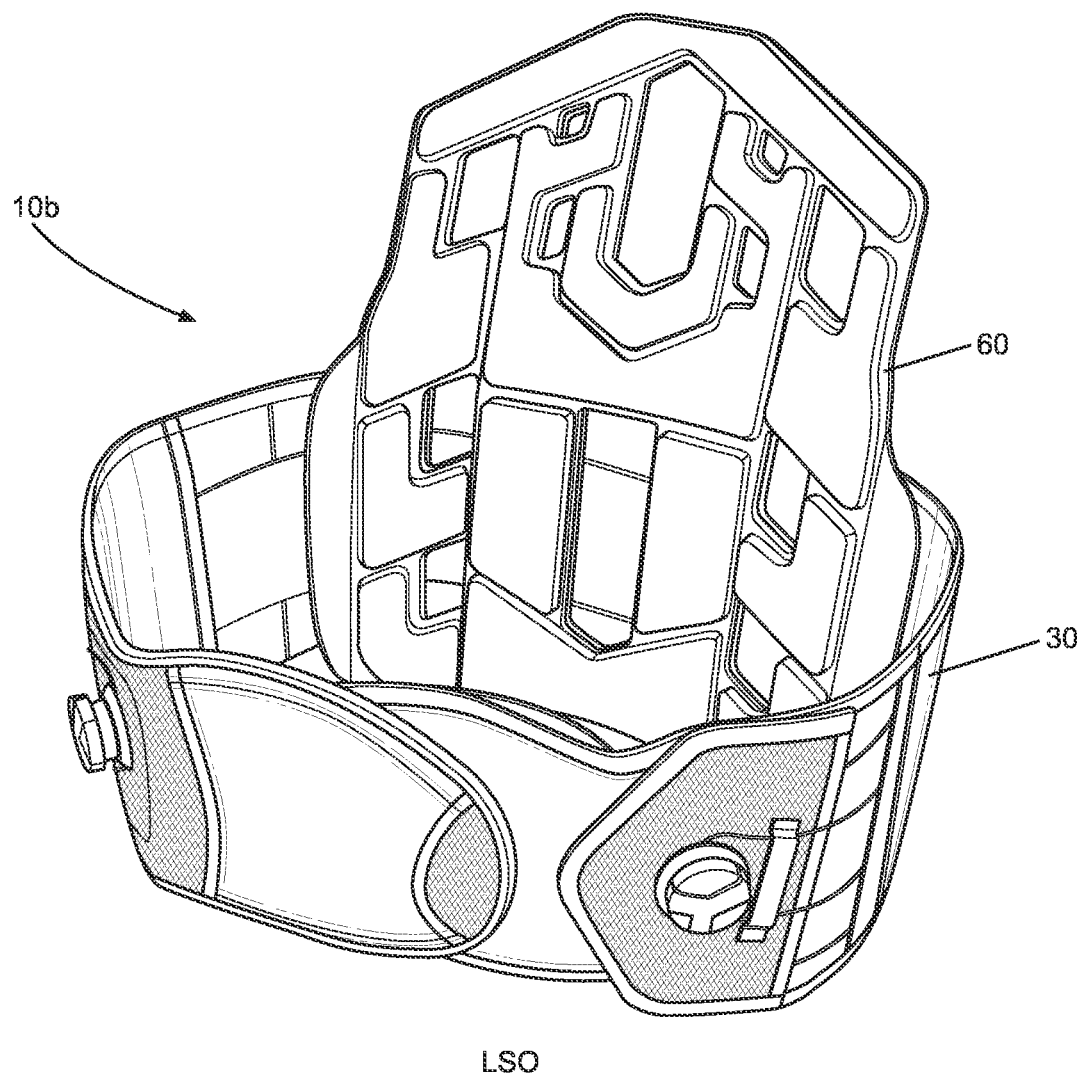

FIGS. 10A-10C show the LSO spinal brace configuration 10b. As shown, it includes only the belt 30 and the posterior panel 60.

FIGS. 11A-11B show conversion from the LSO spinal brace configuration 10b to the TLSO-D spinal brace configuration 10c. As shown, this involves installation of the dorsal lumbar extension 80 onto the posterior panel 60.

Figure 12A:
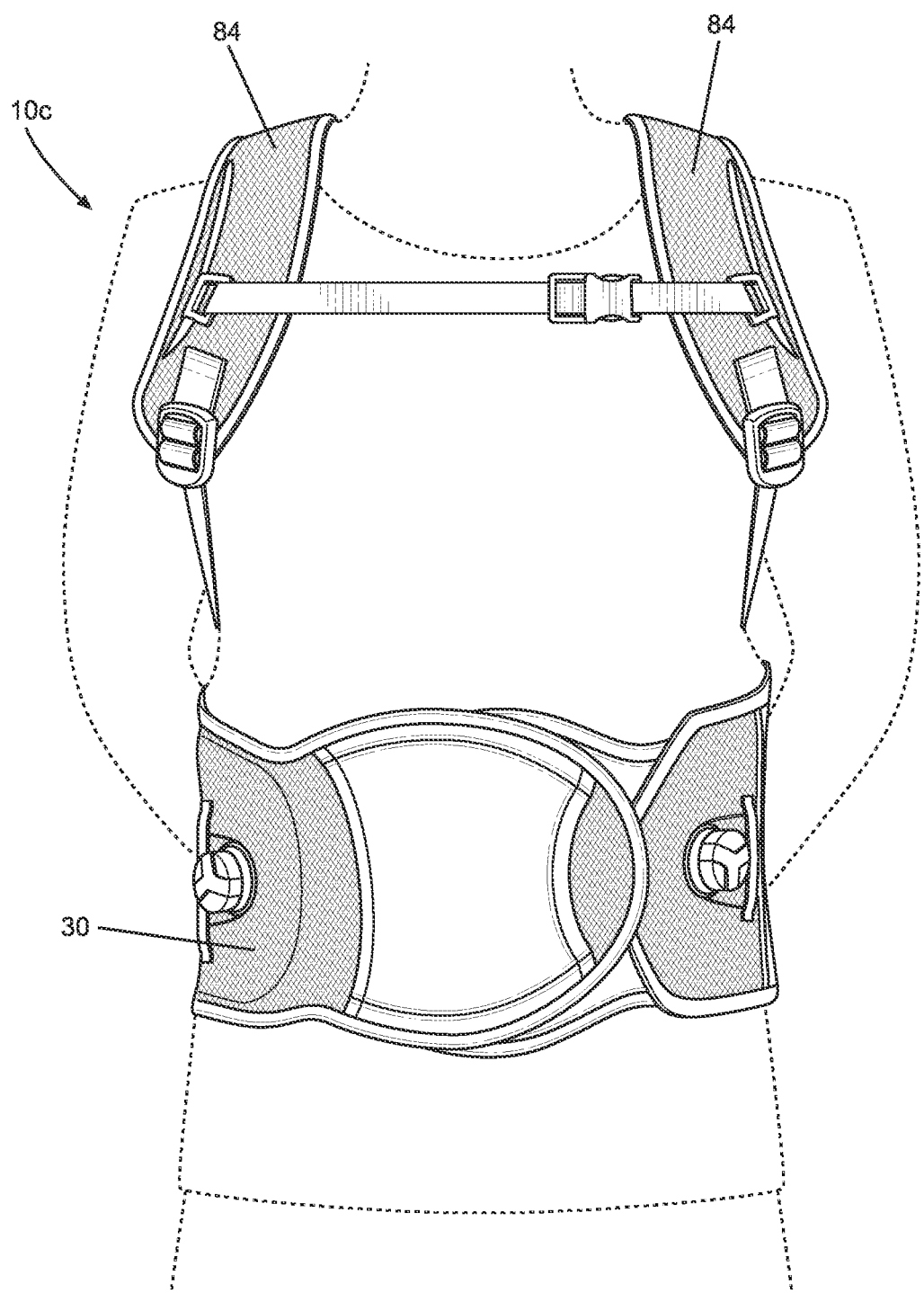
FIGS. 12A-12C show the brace in the TLSO-D configuration.
Figure 12B:
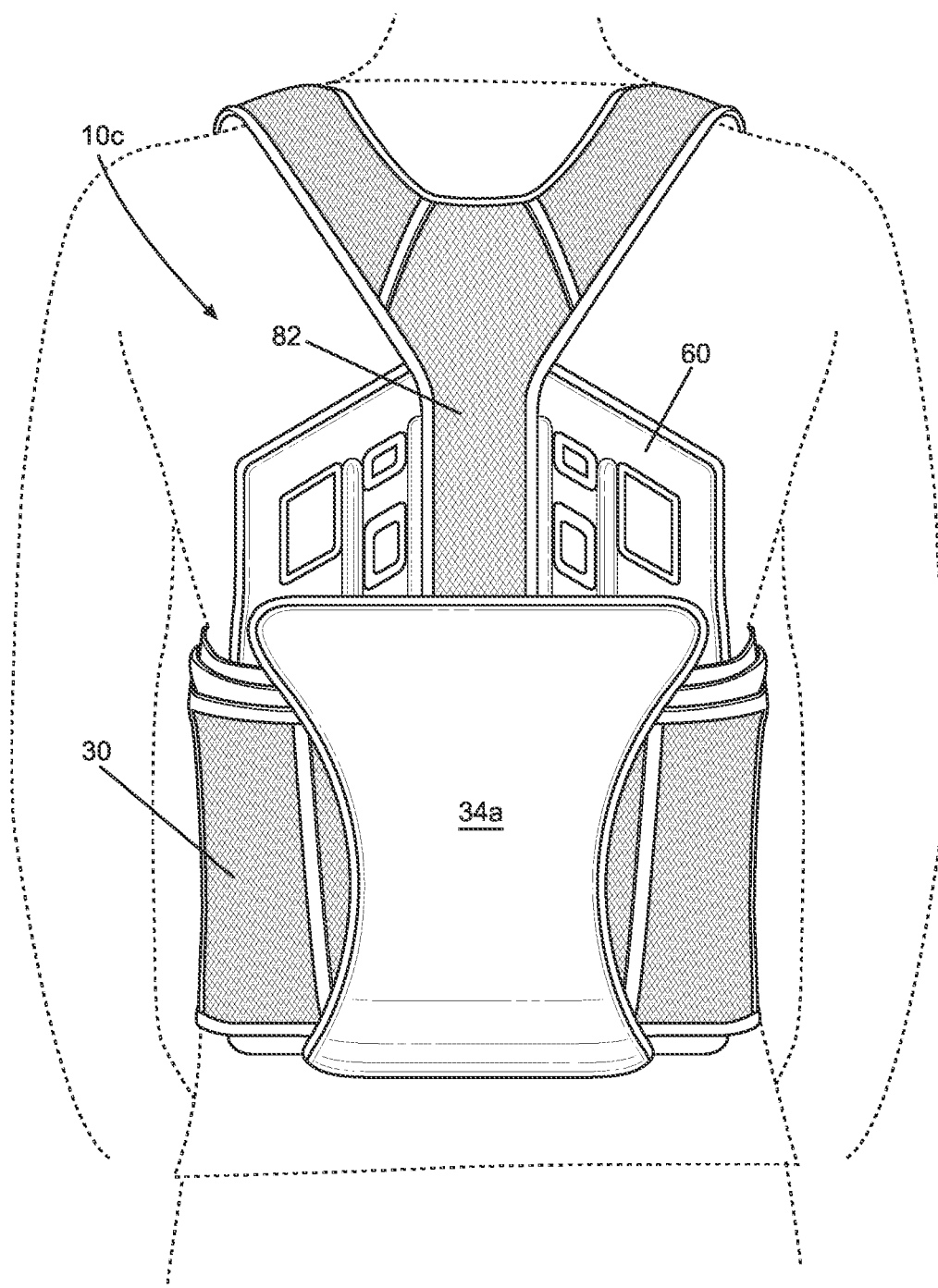
Figure 12C:
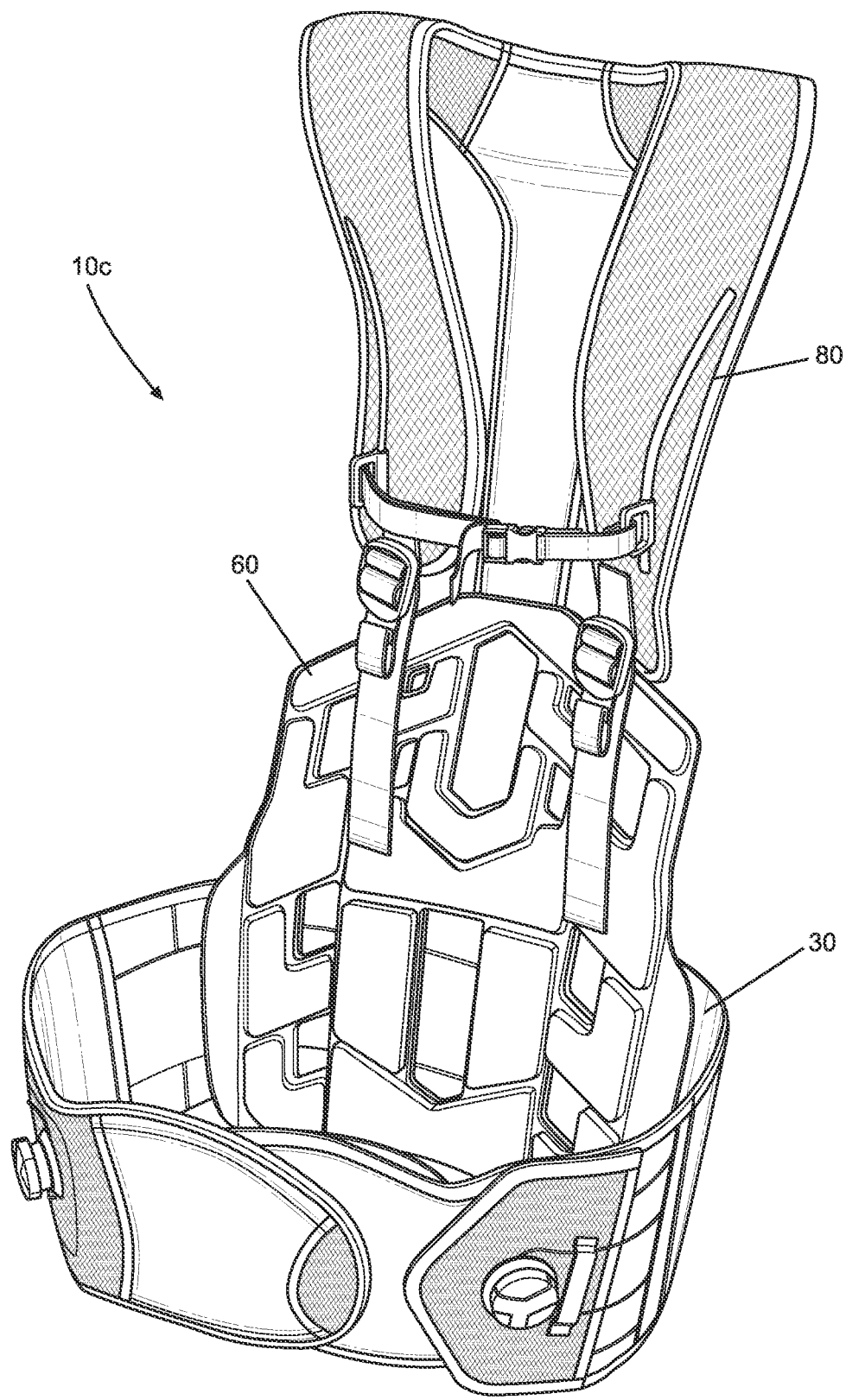

FIGS. 12A-12C show the TLSO-D spinal brace configuration 10c. As shown, it includes only the belt 30, the posterior panel 60, and the dorsal lumbar extension 80.

The brace system 10 therefore advantageously enables multiple configurations and each of these configurations enables for use as an inventory stock-keeping unit (SKU). For example, it has been discovered that the brace system 10 enables the use of only three different SKU's for configurations effective to treat over 90 percent of patient conditions. For example, the LSO spinal brace configuration 10b may be selected for most L5-S1 pathologies, the TLSO-D 10c spinal brace configuration may be selected for most T6-S1 pathologies, and the TLSO-S spinal brace configuration 10a may be selected for most T6-S1 pathologies.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated.

The invention claimed is:
1. A method for providing and configuring a spinal brace between an LSO spinal brace configuration, a TLSO-D spinal brace configuration, and a TLSO-S spinal brace configuration, the method comprising the steps:

provinding spinal brace components that may be selectively utilized in various combinations to provide an LSO spinal brace configuration, a TLSO-D spinal brace configuration, or a TLSO-S spinal brace configuration, the components comprising: a pair of individual lateral panels, an adjustable belt, an anterior panel having a sternal pad kit, a posterior panel having a removable posterior thoracic extension, and a removable dorsal lumbar extension;

assembling the spinal brace components into the TLSO-S spinal brace configuration comprising, the anterior panel and the posterior panel, with the pair of individual lateral panels bridging between the anterior panel and the posterior panel, and the adjustable belt tightenable around the anterior, posterior, and lateral panels, with the posterior thoracic extension attachable to the posterior panel or the dorsal lumbar extension attached to the posterior panel; and then selectively converting the TLSO-S spinal brace configuration into the LSO spinal brace configuration or the TLSO-D spinal brace configuration; and converting the TLSO-S spinal brace configuration to the LSO spinal brace of the TLSO-D spinal brace configuration, wherein to convert the TLSO-S spinal brace configuration to the LSO spinal brace configuration, the sternal pad kit and the posterior thoracic extension are removed, followed by removal of the lateral panels and the anterior panel, wherein to convert the TLSO-S spinal brace configuration to the TLSO-D spinal brace configuration, the sternal pad kit and the posterior thoracic extension are removed, followed by removal of the lateral panels and the anterior panel, and then installing the dorsal lumbar extension onto the posterior panel.

2. The method of claim 1, wherein the posterior panel includes anchor points and the dorsal lumbar extension includes straps that may be adjustably anchored to the anchor points.

* * * * *